United States Patent
Amighi et al.

(10) Patent No.: US 12,239,708 B2
(45) Date of Patent: Mar. 4, 2025

(54) DRY POWDER INHALATION FORMULATION AND ITS USE FOR THE THERAPEUTIC TREATMENT OF LUNGS

(71) Applicant: UNIVERSITÉ LIBRE DE BRUXELLES, Brussels (BE)

(72) Inventors: Karim Amighi, Brussels (BE); Nathalie Wauthoz, Brussels (BE); Rémi Rosière, Brussels (BE)

(73) Assignee: UNIVERSITÉ LIBRE DE BRUXELLES, Brussels (BE)

( * ) Notice: Subject to any disclaimer, the term of this patent is extended or adjusted under 35 U.S.C. 154(b) by 745 days.

(21) Appl. No.: 17/295,610

(22) PCT Filed: Dec. 27, 2019

(86) PCT No.: PCT/EP2019/087122
§ 371 (c)(1),
(2) Date: May 20, 2021

(87) PCT Pub. No.: WO2020/136276
PCT Pub. Date: Jul. 2, 2020

(65) Prior Publication Data
US 2022/0016247 A1 Jan. 20, 2022

(30) Foreign Application Priority Data

Dec. 28, 2018 (EP) .................................... 18248302

(51) Int. Cl.
*A61K 47/14* (2017.01)
*A61K 9/00* (2006.01)
*A61K 45/06* (2006.01)

(52) U.S. Cl.
CPC ............ *A61K 47/14* (2013.01); *A61K 9/0075* (2013.01); *A61K 45/06* (2013.01)

(58) Field of Classification Search
CPC ....... A61K 47/14; A61K 9/0075; A61K 45/06
See application file for complete search history.

(56) References Cited

U.S. PATENT DOCUMENTS

| | | | |
|---|---|---|---|
| 9,724,382 B2 | 8/2017 | Keller et al. | |
| 2005/0042178 A1* | 2/2005 | Trunk | A61K 9/0075 514/17.7 |
| 2014/0065219 A1 | 3/2014 | Bosch et al. | |

FOREIGN PATENT DOCUMENTS

| | | | |
|---|---|---|---|
| KR | 10-2015-0041608 | 4/2015 | |
| WO | 2007/068443 A1 | 6/2007 | |
| WO | WO-2013128283 A2 * | 9/2013 | ............... A61J 3/02 |

OTHER PUBLICATIONS

Levet et al, Development of controlled-release cisplatin dry powders for inhalation against lung cancers, Int. J. Pharm., vol. 515, Issues 1-2, Dec. 30, 2016, pp. 209-220) (Year: 2016).*

(Continued)

*Primary Examiner* — Benjamin J Packard
*Assistant Examiner* — Joshua A Atkinson
(74) *Attorney, Agent, or Firm* — CHRISTENSEN O'CONNOR JOHNSON KINDNESS PLLC

(57) ABSTRACT

A dry powder inhalation formulation includes at least one active pharmaceutical ingredient (API) and a lipid matrix having at least one triglyceride chosen in the group consisting of monohydroxystearin, dihydroxystearin, trihydroxystearin and their mixture and its manufacturing method.

21 Claims, 9 Drawing Sheets

(56) References Cited

OTHER PUBLICATIONS

DeWolf Chemical, CUTINA HR Powder, 2016. Retrieved from: https://web.archive.org/web/20160502000305/https://dewolfchem.com/shop/cutina-hr-powder/ (Year: 2016).*

Cayman Chemical, Salbutamol Product Information, 2022. (Year: 2022).*

Office Action mailed Jul. 11, 2023, issued in corresponding Russian Application No. 2021118740, filed Dec. 27, 2019, 12 pages.

Office Action mailed Jul. 4, 2023, issued in corresponding Japanese Application No. 2021-538005, filed Dec. 27, 2019, 5 pages.

Office Action mailed Jul. 15, 2023, issued in corresponding Chinese Application No. 2019800864565, filed Dec. 27, 2019, 7 pages.

International Search Report mailed Apr. 20, 2020, issued in corresponding International Application No. PCT/EP2019/087122, filed Dec. 27, 2019, 5 pages.

Written Opinion of the International Searching Authority mailed Apr. 20, 2020, issued in corresponding International Application No. PCT/EP2019/087122, filed Dec. 27, 2019, 7 pages.

Levet, V. et al., "Platinum pharmacokinetics in mice following inhalation of cisplatin dry powders with different release and lung retention properties", International Journal of Pharmaceutics, (517)1, Dec. 2016, pp. 359-372, XP029878094.

Levet, V. et al., "Development of controlled-release cisplatin dry powders for inhalation against lung cancers", International Journal of Pharmaceutics, (515)1-2, Oct. 2016, pp. 209-220, XP055584532.

Depreter, F. and Amighi, K., "Formulation and in vitro evaluation of highly dispersive insulin dry powder formulations for lung administration", European Journal of Pharmaceutics and Biopharmaceutics, (76) 3, Nov. 2010, pp. 454-463, XP027503473.

Sebti, T. and Amighi, K., "Preparation and in vitro evaluation of lipidic carriers and fillers for inhalation", European Journal of Pharmaceutics and Biopharmaceutics, (63)1, May 2006, pp. 51-58, XP027998019.

Pilcer, G. and Amighi, K., "Formulation strategy and use of excipients in pulmonary drug delivery", International Journal of Pharmaceutics, Elsevier, NL, (392)1-2, Jun. 2010, pp. 1-19, XP027044497.

Singapore Search Report and Written Opinion mailed Aug. 31, 2022 and Sep. 2, 2022, issued in corresponding Singapore Application No. 11202105291Q, filed on Dec. 27, 2019, 7 pages.

Korean Office Action mailed Oct. 24, 2024, issued in corresponding Korean Patent Application No. 10-2021-7023776, filed Jul. 26, 2021, 20 pages.

* cited by examiner

DRY POWDER INHALATION FORMULATION AND ITS USE FOR THE THERAPEUTIC TREATMENT OF LUNGS

FIELD OF THE DISCLOSURE

The present disclosure relates to a dry powder inhalation formulation and its use for the therapeutic treatment of lungs.

BACKGROUND

Dry powder inhalation (DPI) therapy is now largely used for delivering many treatments to the lungs, such as for example in the treatment of asthma and many efforts have been done to optimize the dry powder inhalation formulations to prolong the retention of the active pharmaceutical ingredient (API) in the lungs.

Inhalation allows the administration of high drug doses directly to lung without prior distribution in the organism. This allows on one side a lower quantity of active pharmaceutical ingredient (API) to be used and likely wasted in the organism, but also, when toxicities of the API are concerned, direct in situ administration allows to lower the toxicities.

Moreover, inhalation is a promising route of administration to deliver API to systemic circulation as the lungs are characterized by an enormous surface of absorption.

However, conventional immediate-release dry powder inhalation (DPI) formulations might nevertheless lead to too short residence in the lungs due to multiple mechanisms of clearance against exogenous inhaled particles (i.e. mucociliary and macrophage clearances) and fast dissolution of drug particles leading to rapid absorption to systemic circulation. This short residence therefore requires multiple dose administrations leading to poor patient compliance. An immediate API release might also be responsible for poor local tolerance because of the fast dissolution of drug particles and high peak concentrations of the API in lung fluids after lung deposition.

Specific excipients have been identified to prolong the retention in the lungs for a sustainable retention profile of the API in the lungs.

There is therefore a need to develop further dry powder inhalation formulations to increase the effectiveness of lung therapies.

In that context, for example, controlled-release cisplatin-based DPI formulations were developed with high drug loading and high fine particle fraction (Levet et al, Int J Pharm 2016). The formulations presented controlled-release and prolonged lung retention abilities leading to low systemic distribution (Levet et al, Int J Pharm 2017).

To this end, Levet et al. have worked on a specific formulation for one anti-neoplastic agent, i.e. cisplatin comprising PEGylated excipients for avoiding too fast elimination by the lung epithelium defense mechanism and have also compared different carrier, such as polymers and lipid matrix to allow for a prolonged retention time in the lungs, thereby increasing efficiency of the inhalation.

Amongst other, the lipid matrix described in the works of Levet et al. comprises tristearin which was identified as a promising candidate for providing the lipid matrix.

Further, even of lipid derived excipient for forming the matrix are preferred over polymers, for toxicity reason, only a few substances able to form a lipid matrix are allowed and accepted for pharmaceutical composition to be inhaled, compared to other route of therapeutic treatment (Pilcer et Amighi, Int J Pharm 2010).

Unfortunately, while tristearin was identified as a promising candidate, its availability on the market is rather limited as a pharmaceutical compound.

SUMMARY

The present disclosure encounters to solve at least a part of these drawbacks by providing a dry powder inhalation formulation for example to be used in a monotherapy or polytherapy, comprising at least one active pharmaceutical ingredient (API) and a lipid matrix comprising at least one triglyceride chosen in the group consisting of monohydroxystearin, dihydroxystearin, trihydroxystearin and their mixture.

It has been surprisingly identified that the at least one triglyceride chosen in the group comprising monohydroxystearin, dihydroxystearin, trihydroxystearin and their mixture, for which a pharmaceutical grade exist, are able to form the lipid matrix with the API (active pharmaceutical ingredient) and showed increased pulmonary deposition rates in the lung, which latter is allowed to be used for lung inhalation.

Indeed, monohydroxystearin, dihydroxystearin, trihydroxystearin and their mixture are compounds having physicochemical properties such as having values of Log P higher than 5, preferably comprised between 14 and 25, more particularly between 18 and 25 and preferably around 20, as measured using the shake-flask method and/or having a melting point temperature higher than or equal to 40° C., preferably higher than or equal to 60° C., more preferably higher than or equal to 75° C.

This allows to produce an inhaled formulation under the form of a dry powder and neither an oil phase, nor a sticky paste for proper use on a dry powder inhaler.

Further, according to the present disclosure, it has been identified against all expectations that it was made possible to increase the pulmonary deposition rate of the API with respect to other conventional triglycerides, such as tristearin and to provide modulated dissolution profile of the API by varying the ratio between the amount of API and the amount of at least one triglyceride chosen in the group comprising monohydroxystearin, dihydroxystearin, trihydroxystearin and their mixture, which was not the case for conventional triglycerides.

Preferably, the dry powder inhalation formulation according to the present disclosure presents a weight ratio between the at least one API and the at least one triglyceride: API/triglyceride comprised between 0.1/99.9 and 99.9/0.1, preferably between 10/90 and 88/12, preferably between 15/85 and 85/15, preferably between 25/75 and 75/25, more preferably between 30/70 and 70/30, in particular between 40/60 and 60/40, such as for example around 50/50.

Advantageously, in the formulation according to the present disclosure, wherein the at least one triglyceride is hydrogenated castor oil.

Castor oil has been described in the literature in long lists of common excipient (see US 2005/0042178) or of milling aid (WO2013/128283).

In a preferred embodiment according to the present disclosure, the dry powder inhalation formulation comprises from 0.1 wt % to 98 wt % of the at least one API with respect to the total weight of the dry powder inhalation formulation. In a first particular embodiment according to the present disclosure, the active agent is a small chemical molecule having a solubility in alcohols of at least 0.1 w %/v, or at least 0.5 w %/v, more preferably of at least 1 w %/v, more particularly of at least 5 w %/v. According to this first particular embodiment, the small chemical molecule is any active pharmaceutical ingredient (API) having a solubility in alcohols of 0.1% w/v or more, defined in the disclosure as an alcohol-soluble API, such as for instance budesonide, paclitaxel, pemetrexed, itraconazole, voriconazole, clarithromycin, salbutamol, salbutamol sulfate, fluticasone, beclomethasone, mometasone, mometasone furoate, ciclesonide, formoterol, arformoterol, indacaterol, indacaterol maleate, olodaterol, olodaterol hydrochloride, salmeterol, ipratropium bromide, glycopyrronium bromide, tiotropium bromide, umeclidinium bromide, ibuprofen, vancomycin, vancomycin hydrochloride, tetrahydrolipstatin, isoniazid, rifampicin, pyrazinamide, docetaxel, vincristine, vincristine sulfate, etoposide, vinorelbine, gemcitabine, . . .

More particularly, a dry powder inhalation formulation according to the first particular embodiment contains from 0.1 wt % to 95 wt %, preferably from 1 wt % to 90 wt %, more preferably from 1 wt % to 85 wt % of the at least one API with respect to the weight of the dry powder inhalation formulation.

In a preferred embodiment according to the present disclosure, the dry powder inhalation formulation consist in lipid matrix particles in which the alcohol-soluble API is dissolved or finely dispersed.

In a second particular embodiment according to the present disclosure, the active agent is a small chemical molecule having a solubility in alcohols less than 0.5 w %/v. In this second particular embodiment, the small chemical molecule is any API having a solubility in alcohols of less than 0.5% w/v, particularly of less than 0.1% w/v and more particularly of less than 0.01% w/v defined as an alcohol-insoluble API, such as for instance cisplatin, carboplatin, oxaliplatin, pemetrexed disodium, azacytidine, beclomethasone dipropionate, tobramycin, aclidinium bromide, . . .

More particularly, a dry powder inhalation formulation according to the second particular embodiment contains from 0.1 wt % to 95 wt %, preferably from 1 wt % to 90 wt %, more preferably from 1 wt % to 85 wt % of the at least one API with respect to the weight of the dry powder inhalation formulation.

Accordingly, the dry powder inhalation formulation comprises from 0.1 wt % to 95 wt % of the alcohol-insoluble API, preferably 1 wt % to 90 wt %, more preferably 1 wt % to 85 wt %, such as for example from 1 wt % to 60, or from 1 to 50 wt % with respect to the total weight of the dry powder inhalation formulation.

In a preferred embodiment according to the present disclosure, the dry powder inhalation formulation consist in lipid matrix particles in which the alcohol-insoluble API is dispersed.

In a third particular embodiment according to the present disclosure, the active agent is a macromolecule. In this third particular embodiment according to the present disclosure, the dry powder inhalation formulation comprises from 0.1 wt % to 95 wt %, preferably from 1 wt % to 90 wt %, more preferably from 1 wt % to 85 wt % of the at least one API with respect to the weight of the dry powder inhalation formulation.

Accordingly, the dry powder inhalation formulation comprises from 0.1 wt % to 95 wt % of the macromolecule, preferably 1 wt % to 90 wt %, more preferably 1 wt % to 85 wt %, such as for example from 1 wt % to 60, or from 1 to 50 wt % with respect to the total weight of the dry powder inhalation formulation.

In yet another preferred embodiment, the formulation according to the present disclosure further comprising a prolonged lung retention excipient such as a PEGylated excipient or polysaccharides such as chitosan or dextran.

Preferably, according to the present disclosure, the prolonged lung retention excipient is PEGylated excipient and is present at an amount comprised between 0.1 wt % to 20 wt %, preferably between 0.2 and 10 wt %, more preferably between 0.5 and 5 wt % relative to the total weight of the dry powder inhalation formulation.

More particularly according to the present disclosure, wherein the PEGylated excipient is derived from vitamin E or from phospholipids, such as tocopheryl polyethylene glycol succinate (TPGS) or distearoyl phosphoethanolamine polyethylene glycol 2000 (DSPE-mPEG-2000).

In yet another preferred embodiment, the formulation according to the present disclosure further comprising one or more excipient, such as excipient that improves physicochemical and/or aerodynamic properties of the dry powder for inhalation.

By the terms "one or more excipient", it is meant a compound selected from sugar alcohols; polyols (such as sorbitol, mannitol and xylitol); crystalline sugars including monosaccharides (such as glucose, arabinose) and disaccharides (such as lactose, maltose, saccharose, dextrose, trehalose, maltitol); inorganic salts (such as sodium chloride and calcium carbonate); organic salts (such as sodium lactate, potassium or sodium phosphate, sodium citrate, urea); polysaccharides (such as dextran, chitosan, starch, cellulose, hyaluronic acid, and their derivatives); oligosaccharides (such as cyclodextrins and dextrins); titanium dioxide; silicone dioxide; magnesium stearate; lecithin; amino acids (such as leucine, isoleucine, histidine, threonine, lysine, valine, methionine, phenylalanine); derivatives of an amino acid (such as acesulfame K, aspartame); lauric acid or derivatives (such as esters and salts); palmitic acid or derivatives (such as esters and salts); stearic acid or derivatives (such as esters and salts); erucic acid or derivatives (such as esters and salts); behenic acid or derivatives (such as esters and salts); sodium stearyl fumarate; sodium stearyl lactylate; phosphatidylcholines; phosphatidylglycerols; natural and synthetic lung surfactants; lauric acid and its salts (such as sodium lauryl sulphate, magnesium lauryl sulphate); triglycerides; sugar esters; phospholipids; cholesterol; talc.

In certain preferred embodiments, the excipient is mannitol, dextran, or lactose.

In certain preferred embodiments, the excipient is phospholipids or cholesterol.

In certain preferred embodiments, the excipient is mannitol, dextran, hyaluronic acid, lactose, phospholipids, or cholesterol.

In certain preferred embodiments, the excipient is mannitol, dextran, phospholipids, or cholesterol.

In certain embodiments, the at least one excipient is a carrier.

In one preferred embodiment of the formulation according to the present disclosure, the formulation in under the form of fine particles having a geometric particle size distribution (PSD) $d_{50}$ lower than or equal to 30 μm, preferably lower than 15 μm, preferably lower than or equal to 10 μm, preferably lower than or equal to 5 μm.

In a further preferred embodiment of the formulation according to the present disclosure, the formulation is under the form of fine particles having a geometric particle size distribution (PSD) $d_{90}$ lower than or equal to 60 μm, preferably lower than or equal to 30 μm, more preferably lower than or equal to 15 μm, preferably lower than or equal to 10 μm and more preferably lower than or equal to 7 μm.

In yet a further preferred embodiment of the formulation according to the present disclosure, the formulation has is under the form of particles having a volume mean diameter D[4,3] lower than or equal to 40 µm, preferably lower than or equal to 20 µm, more preferably lower than or equal to 15 µm, preferably lower than or equal to 10 µm, preferably lower than or equal to 6 µm.

Preferably, according to the present disclosure, the improving excipient and/or the excipient is present at an amount comprised between 0.1% w/w and 80 wt %, preferably lower than 70 wt %, more preferably lower than 60 wt %, in particular lower than 50 wt %, such as lower than 50 wt % relative to the total weight of the dry powder inhalation formulation.

The term "fine particle dose" or "FPD" generally refers to the mass of the particles with an aerodynamic diameter below 5 µm relative to the mass of the nominal dose (i.e. the mass of the dose loaded in the inhalation device).

The fine particle dose or fine particle fraction represents the fraction of the pharmaceutical formulation that can be deeply inhaled and is theoretically available for pharmacological activity (Dunbar et al, Kona 16: 7-45, 1998).

In an advantageous embodiment according to the present disclosure, the formulation in under the form of fine particles having a mass median aerodynamic diameter (MMAD) lower than or equal to 6 µm, preferably lower than or equal to 5 µm, preferably lower than or equal to 4 µm.

The MMAD refers to the diameter of the particles deposited in an impactor for which 50% (w/w) of particles have a lower diameter and 50% (w/w) have a higher diameter.

The terms "aerodynamic diameter" or "dae" of a particle may be defined as the diameter of a sphere with a unit density (i.e., density of 1) that has the same settling velocity in still air as the particle in consideration. The "dae" provides a useful measurement of inhalable particles and takes into account factors that affect their aerodynamic properties. "Dae" can be used to compare particles of differing physical size and takes into account their density and shape as well as their geometric size.

Methods for measuring "dae" are methods described in the European or US Pharmacopeas using an impactor or impaction apparatus such as glass impinger, multi-stage liquid impinger (MsLI), Andersen cascade impactor, or next-generation impactor (NGI). These allow the aerodynamic properties of DPI formulations (including MMAD, geometric standard deviation, lung deposition pattern, fine particle dose, fine particle fraction) to be measured under simulated breathing conditions.

The total dose of particles with aerodynamic diameters smaller than 5 µm can be calculated by interpolation from the collection efficiency curve and considered as the fine particle dose (FPD) or fine particle fraction (FPF), expressed as a percentage of the nominal API dose (i.e. the dose contained in the DPI device).

Preferably, the dry powder inhalation formulation according to the present disclosure, is packaged in, for example a blister or a capsule, to be used in a dry powder inhaler or in a hermetical and/or disposable dry powder inhaler.

In a specific embodiment, the active agent is a small chemical molecule having a bronchodilator activity, a glucocorticoid, an anti-inflammatory activity, an anti-infection activity (e.g. antibiotics, anti-tuberculous, antifungal, antiviral), . . .

In another specific embodiment, the small chemical molecule is any active pharmaceutical ingredient absorbed by the lung for a systemic or a local therapy, such as for instance, budesonide, salbutamol, fluticasone, beclomethasone, mometasone, ciclesonide, formoterol, salbutamol, arformoterol, indacaterol, olodaterol, salmeterol, ipratropium, aclidinium, glycopyrronium, tiotropium, unmeclidinium, mometasone, ciclesonide, formoterol, arformoterol, ibuprofen, tobramycin, vancomycin, tetrahydrolipstatin, clarithromycin, isoniazid, rifampin, pyrazinamide, itraconazole, voriconazole, aztreonam, ethambutol, streptomycin, kanamycin, amikacin, colistin, colistimethate sodium, capreomycin, ciprofloxacin, rifapentine, doxycycline, cycloserine E, ethionamide, gatifloxacin, levofloxacin, moxifloxain, ofloxacin, fosfomycin, p-aminosalycylate, Denufosol tetrasodium, Lancovutide, Ribavirin, zanamivir, laminavir, rupintrivir, Pentamidine, amphotericin B, posaconazole, isavuconazole, capsufungin, micafungin, anidulafangin, Iloprost, levothyroxine, their salts, solvates, hydrates, polymorph forms and the esters thereof, their combination, analogs and derivates.

In yet further embodiment, the active agent is a macromolecule such as a peptide, a protein, an antibody, an antibody fragment, a nanobody, a nucleic acid.

Preferably, said according to the present disclosure, the macromolecule is insulin, proinsuline, synthetic insulin, semi-synthetic insulin, bevacizumab, pembrolizumab, atezolizumab, nivolumab, ipilimumab, toll-like receptor agonists, ghrelin, IgG monoclonal antibody, a small interfering ribonucleic acid (siRNA), Dornase alfa, Ciclosporin A, Alpha-1 antitrypsin, interleukin antagonists, Interferon-$\alpha$, Interferon-$\beta$, Interferon-$\gamma$, Interferon-$\omega$, Interleukin-2, Anti-IgE mAb, Catalase, Calcitonin, Parathyroid hormone, Human growth hormone, Insulin-like growth factor-I, heparin, rhG-CSF, GM-CSF, Epo-Fc, FSH-Fc, sFc-$\gamma$ RIIb, mRNA.

In a further preferred embodiment, the active agent is an anti-neoplastic agent, for example to be provided for lung cancer and lung tumors.

Lung cancer is the cancer with the highest prevalence and mortality in the world. In most cases, lung cancer is diagnosed at advanced stages. Therefore, the patients often present already metastases in the lungs or in other organs, i.e. extrapulmonary metastases. Treatment modalities are mostly used in combination and consist in surgery, radiotherapy, chemotherapy, targeted therapy and immunotherapy.

Chemotherapy is used in up to 60% of lung cancer patients, mainly in advanced stages of the disease. Chemotherapy is currently administered through intravenous injection or infusion or per os, i.e. systemic routes of administration, i.e. systemic chemotherapy. Chemotherapy is responsible for severe systemic toxicities due to (i) the broad distribution of the chemotherapeutic in the organism and (ii) the lack of selectivity for cancer cells. Oncologists are consequently in great need for new more efficient and better-tolerated treatment approaches.

Chemotherapy is indeed a matter of finding the highest amount of anti-neoplastic agent to be administered by reducing at a maximum level the non-reversible toxicity side effects and disagreeable side effects generated by the chemotherapy.

Accordingly, very complex therapeutic scheme is foreseen combining very often different therapeutic treatments and acts, such as for example, surgery, with a first cycle of radiotherapy, followed by complex cycles of anti-neoplastic agent injections or intravenous infusion, which can be the same or different for each cycle and reduced or adapted depending on the side effect identified on the body of the patient.

Each anti-neoplastic agent or molecule has a dose limiting toxicity (DLT) such as nephrotoxicity, neurotoxicity, . . . which require to introduce in the therapeutic scheme rest period(s) allowing the patient body to recover from the adverse side effects, when not non-reversible.

Further, anti-neoplastic agent has a half-life period being often is known as its half-life. The half-life time period is the period of time required for the concentration or amount of drug in the body to be reduced by one-half. The half-time period of anti-neoplastic agent is typically comprised between 12 hours and 36 hours, which can be short as representing the exposition time of the human body to the beneficial effect of the anti-neoplastic agent.

However, due to the dose limiting toxicity (DLT) of anti-neoplastic agent, the amount of administered doses during several administering periods remains limited and should be separated one to each other, as said previously, by rest- or off-period.

The combination of the half-life period together with the dose limiting toxicities, together with the fact that when the anti-neoplastic agent is administered by oral or injection or intravenous infusion, has the consequence that the concentration of the anti-neoplastic agent which reach efficiently the solid tumor site is low, with limited effect on the tumor itself and high systemic toxicity for the patient body.

Further another constrain of anti-neoplastic agent is the cumulative dose which is the total dose resulting from repeated exposures to the anti-neoplastic agent of the same part of the body or of the whole body.

For cisplatin, administered through intravenous route, the cumulative dose is 300 mg/m$^2$ within 4 to 6 cycles.

Those considerations yielded researchers of the present disclosure to develop more targeted therapies and on-site injection/infusions.

Inhaled therapy is of different kind and one can distinguish nebulizers form inhalers as distinct manner to deliver APIs to the respiratory tract. Inhalers can also be of different type and dry powder inhalers (DPI) are one of them.

Compared to nebulizers, dry powder inhalers (DPI) are well-adapted to chemotherapy. They allow high doses of APIs, but also poorly water-soluble compounds (i.e. most chemotherapeutics in cancer) to be administered. Moreover, DPI limit environmental contamination by the aerosol due to (i) their activation and drive by the patient's inspiratory flow only and (ii) negligible exhaled drug doses. Finally, DPI can be designed as single-use disposable devices.

There is therefore a need to develop pulmonary route for anti-neoplastic agent and to adapt deeply current inhalation devices and formulations used in clinical trials to deliver effective anticancer therapies to tumor-bearing lungs.

There are many advantages to prolong the retention profile of the antineoplastic agent in the lungs and make sure absorption is not too fast. However, reaching prolonged release profile remains challenging nowadays as the absorption surface area of lung is incredibly high, thereby resulting in a fast systemic absorption of the agent.

As explained previously, controlled-release cisplatin-based DPI formulations were developed with high drug loading and high fine particle fraction having controlled-release and prolonged lung retention abilities leading to low systemic distribution. (Levet et al, Int J Pharm 2017). According to this document, in a lung cancer mice model, this approach led to comparable tumor response in vivo than the intravenous regimen at half dose (1.0 mg/kg vs 0.5 mg/kg, respectively). The intravenous regimen gives good results for extrapulmonary metastases while inhaled cisplatin seemed more active against pulmonary tumors.

DPI formulations composed of paclitaxel-based nanocarriers were also developed with increased residence time in the lungs, limited systemic distribution and aimed specifically at lung cancer cells by targeting the folate receptor (FR) (Rosiere et al, Int J Pharm 2016; Rosiere et al, Mol Pharm, 2018). FR, especially FR-a, is overexpressed on the cancer cell surfaces in many lung tumors (i.e. more than 70% of adenocarcinomas) and is a promising membrane receptor to target in lung cancer. Significantly longer survival rates were observed for the FR-targeted inhaled treatments in combination with intravenous Taxol® (the commercial form of paclitaxel), than for intravenous Taxol® alone in a lung cancer mice model.

To resume, although the use of DPI chemotherapy led to encouraging preclinical results in terms of pharmacokinetic profiles and safety, their efficacy is still rather limited.

Although numerous advantages can be derived from reaching a prolonged release profile for the anti-neoplastic agent, in the context of inhaled chemotherapy, this challenge is even accentuated as lungs present a significant huge absorption surface causing the API to be quickly absorbed and provided to the systemic circulation.

Further, because lungs are provided with strong defense mechanisms, the elimination of the API in inhaled therapy is quite quick due to highly efficient clearance mechanisms in the lungs against foreign deposited particles.

Sebti et al (Sebti et al, Eur J Pharm Biopharm 2006a; Sebti et al, Eur J Pharm Biopharm 2006b) developed a solid lipid macroparticles with budesonide and a lipid matrix composed of cholesterol but did not observe any delay in budesonide release profile.

To the same end, Depreter et Amighi (Depreter and Amighi, Eur J Pharm Biopharm 2010) developed insulin microparticles coated with a lipid matrix composed of cholesterol for which only a little delay in insulin release was observed.

To the same end, as mentioned previously, Levet et al. have worked to allow for a prolonged retention time in the lungs, thereby increasing efficiency of the inhaled chemotherapy and identified a lipid matrix composed of tristearin and TPGS as a promising candidate.

Further, even if lipid derived excipient for forming the matrix are preferred over polymers, for toxicity reason, only a few substances able to form a lipid matrix are allowed and accepted for pharmaceutical composition to be inhaled, compared to other route of therapeutic treatment (Pilcer and Amighi, Int J Pharm 2010).

Unfortunately, while tristearin-based matrix was identified as a promising, its availability on the market is rather limited as a pharmaceutical compound, while the availability of the at least one triglyceride chosen in the group comprising monohydroxystearin, dihydroxystearin, trihydroxystearin and their mixture is largely broader.

Moreover, the tristearin-based matrix was not promising for controlling the release profile of voriconazole while the preparation method (i.e. spray-drying) and excipient composition were similar as described in Levet et al for cisplatin.

Further, it has been identified according to the present disclosure that the at least one triglyceride chosen in the restricted group according to the present disclosure allows, in addition to obtain a sustained-release profile and a prolonged retention of chemotherapy in the lungs, to increase the pulmonary deposition rate significantly with respect to the closest triglyceride, tristearin.

Preferably, the anti-neoplastic agent is cisplatin, carboplatin, oxaliplatin, docetaxel, paclitaxel, pemetrexed, etoposide, vinorelbine.

Other embodiments of the dry powder inhalation formulations according to the present disclosure are mentioned in the appended claims.

The present disclosure relates to methods for manufacturing a dry powder inhalation formulation according to the present disclosure, comprising the steps of:
a) Mixing the one or more API in a predetermined amount of at least one triglyceride chosen in the group comprising monohydroxystearin, dihydroxystearin, trihydroxystearin and their mixture with or without a solvent,
b) a bottom-up or top-down method leading to inhalable particles from the previous mixture such as a micronisation step such as spray drying a suspension or a solution, spray-congealing a solution of the active drug or API in the at least one triglyceride or an extrusion followed by a jet milling of a physical mixture of the API with the at least one triglyceride.

For instance, the present disclosure relates to a method for manufacturing a dry powder inhalation formulation according to the present disclosure, comprises a step of suspending or solubilizing a powder of one or more API in a predetermined amount of at least one triglyceride chosen in the group comprising monohydroxystearin, dihydroxystearin, trihydroxystearin and their mixture to form a suspension of particles or a solution of one or more API (for example: by melting and/or by extrusion), followed by a size reduction of particles of solution or suspension of one or more API obtained after cooling (e.g. by spray-congealing) or extrusion, at high speed and/or pressure to obtain the dry powder inhalation formulation (for example: by jet milling).

In another instance, the method of manufacturing comprises the steps of:
a) Homogenously mixing at least one API with at least one triglyceride, forming a homogenous mixture,
b) Extruding the homogenous mixture with a (twin-screw) extruder at an appropriated temperature to obtain a homogeneous lipidic matrix containing the API,
c) Cutting the extrudate to obtain coarse pellets/cylinders,
d) Optionally transforming the triglycerides in a stable polymorphic form by storing the coarse pellets/cylinders at appropriate storage conditions, and
e) Milling the pellets by using an appropriate mill to obtain microparticles for inhalation (DPI) containing the API with the at least one triglyceride.

In yet another instance, the present disclosure relates to a method for manufacturing a dry powder inhalation formulation according to the present disclosure, comprising the steps of:
a) Suspending or solubilizing a powder of one or more API in a solvent to form a suspension of particles or a solution of one or more API
b) Optional size reduction of the particles of one or more API at high speed and/or pressure homogenization under cooling to form a suspension of reduced in size particles of one or more API,
c) Mixing a predetermined amount of at least one triglyceride chosen in the group comprising monohydroxystearin, dihydroxystearin, trihydroxystearin and their mixture in a solvent with the microcrystal suspension or solution to obtain a mixture of the at least one API with the at least one triglyceride
d) Spray-drying the mixture of the at least one API with the at least one triglyceride to obtain the dry powder inhalation formulation.

In a preferred embodiment of the method according to the present disclosure, the high speed applied for the size reduction is comprised between 10 000 and 30 000 rpm, preferably between 15 000 and 26 000 rpm and is applied for a time period comprised between 8 and 15 minutes, preferably between 9 and 12 minutes.

Preferably, according to the present disclosure, the high pressure for the homogenization step is increased gradually from a first pressure comprised between 2 000 and 10 000 psi, preferably between 4 000 and 6 000 psi over a predetermined number of pre-milling cycles comprised between 8 and 12, preferably between 9 and 11, to a second pressure comprised between 8 000 and 12 000 psi, preferably between 9 000 and 11 000 psi over a predetermined number of pre-milling cycles comprised between 8 and 12, preferably between 9 and 11, to a third pressure comprised between 18 000 and 24 000 psi, preferably between 19 000 and 22 000 psi over a predetermined number of pre-milling cycles comprised between 18 and 22, preferably between 19 and 21.

In a particularly preferred embodiment according to the disclosure, the microcrystal of the microcrystal suspension has a geometric particle size distribution (PSD) $d_{50}$ lower than or equal to 30 µm, preferably lower than 15 µm, preferably lower than or equal to 10 µm, preferably lower than or equal to 5 µm.

In a further particularly preferred embodiment according to the disclosure the microcrystal of the microcrystal suspension has a geometric particle size distribution (PSD) $d_{90}$ lower than or equal to 60 µm, preferably lower than or equal to 30 µm, more preferably lower than or equal to 15 µm, preferably lower than or equal to 10 µm and more preferably lower than or equal to 7 µm.

In another particularly preferred embodiment according to the disclosure wherein the microcrystal of the microcrystal suspension has a volume mean diameter D[4,3] lower than or equal to 40 µm, preferably lower than or equal to 20 µm, more preferably lower than or equal to 15 µm, preferably lower than or equal to 10 µm, preferably lower than or equal to 6 µm.

In an advantageous preferred embodiment according to the disclosure PEGylated excipients or other excipients are further added.

Other embodiments of the method according to the present disclosure are mentioned in the appended claims The present disclosure further relates to the use of a dry powder inhalation formulation in lung therapy.

Preferably, the use according to the disclosure is foreseen for treating local lung diseases: asthma, COPD, lung infections (e.g. cystic fibrosis patients, aspergillosis, tuberculosis, etc.), or systemic diseases (e.g. diabetes, pain, etc.).

In a variant according to the present disclosure, the dry powder inhaled chemotherapy formulation is used in a polytherapy for the treatment of lung cancer such as any lung tumor, such as pulmonary metastases, for example osteosarcoma metastases, a small cell lung cancer or a non-small cell lung cancer.

Advantageously, the polytherapy comprises one primary therapy chosen in the group consisting of intravenous injection or infusion chemotherapy, immunotherapy, tumor ablative surgery, ablative surgery for removing a part of or a full organ bearing a tumor, a curative surgery, a radiotherapy and their combination and one or more chemotherapy by inhalation as additional therapy.

The present disclosure also related to the corresponding therapeutic method.

DESCRIPTION OF THE DRAWINGS

Other characteristics and advantages of the present disclosure will be derived from the non-limitative following description, and by making reference to the examples and the figures.

In the drawings.

DETAILED DESCRIPTION

Examples

Example 1.—Preparation of Cisplatin Dry Powder Formulation for Inhalation n° 1

Briefly, raw cisplatin microcrystals from bulk powder (Shanghai Jinhe Bio-technology Co., Ltd., Shanghai, PRC) were first suspended in 50 mL isopropanol to reach a concentration of 5% w/v and reduced in size by high-speed (10 min at 24 000 rpm) (X620 motor and a T10 dispersing shaft, IngenieurbOro CAT M. Zipperer GmbH, Staufen, Germany) and high-pressure homogenization (EmulsiFlex-C5 high-pressure homogenizer, Avestin Inc., Ottawa, Canada) at 5 000 psi then 10 000 psi over 10 pre-milling cycles each, then at 20 000 psi over 20 milling cycles. A heat exchanger was connected to the homogenizing valve and maintained at −15° C. using an F32-MA cooling circulator (Julabo GmbH, Seelbach, Germany). An aliquot was removed from the suspension at the end of the process to measure the particle size distribution (PSD) of cisplatin microcrystals by laser diffraction (see below).

Figure 1:
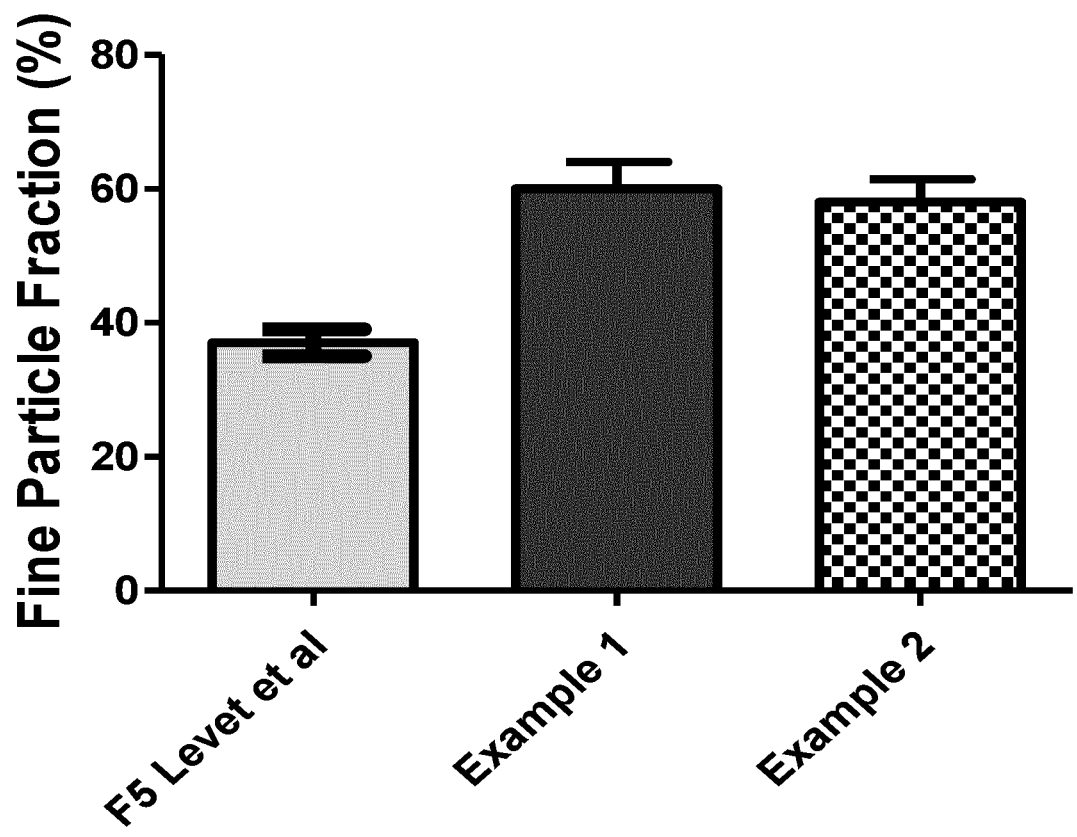
FIG. 1 presents the FPF values (%) of the comparative example (Composition F5 in Levet al) and examples 1 and 2 (mean±SD, n=2-3).

Then, castor oil hydrogenated (BASF, Ludwigshafen, Germany) and TPGS (Sigma-Aldrich, St-Louis, USA) solubilized in heated isopropanol were added to the microcrystal suspension to obtain a final concentration of 1.32% w/v of cisplatin and 0.68% w/v of castor oil hydrogenated/TPGS (99:1 w/w) mixture and spray dried with a Mini-Spray Dryer B-290 (Büchi Labortechnik AG, Flawil, Switzerland) to obtain a DPI formulation for human use.

The operating parameters used during spray-drying were as follows: feed rate 3.0 g/min, inlet temperature 70° C., 0.7 mm nozzle, 1.5 mm nozzle-cap, compressed air at 800 L/min and drying air flow 35 $m^3/h$. The apparatus was equipped with a B-296 dehumidifier (Büchi Labortechnik AG) to maintain the relative humidity at 50% HR during spray-drying.

The geometrical PSD of bulk cisplatin, cisplatin microparticles from the size-reduction process, and cisplatin dry powder formulation, was measured as suspended and individualized particles. This was done using a Mastersizer 3000 laser diffractometer (Malvern Instruments Ltd., Worcestershire, UK) connected to a Hydro MV dispenser equipped with a 40 W ultrasonic probe (Malvern Instruments Ltd.). Measurements of bulk cisplatin and aliquots from the size-reduction process were performed in cisplatin-saturated isopropanol. The cisplatin dry powder formulation was previously dispersed, vortexed and measured in cisplatin-saturated 0.1% w/v Poloxamer 407 (BASF, Ludwigshafen, Germany) NaCl 0.9% aqueous solution. The PSD was expressed as the volume median diameter d(0.5) (for which 50% of particles lie under the expressed diameter), the volume mean diameter D[4,3] and the percentage of fine particles determined from the cumulative undersize curves (% of particles below 5 μm). The PSD results are in the range foreseen according to the present disclosure.

Example 2.—Preparation of Cisplatin Dry Powder Formulations for Inhalation n° 2

Briefly, raw cisplatin microcrystals from bulk powder (Shanghai Jinhe Bio-technology Co., Ltd., Shanghai, PRC) were first suspended in 50 mL isopropanol to reach a concentration of 5% w/v and reduced in size by high-speed (10 min at 24 000 rpm) (X620 motor and a T10 dispersing shaft, IngenieurbOro CAT M. Zipperer GmbH, Staufen, Germany) and high-pressure homogenization (EmulsiFlex-C5 high-pressure homogenizer, Avestin Inc., Ottawa, Canada) at 5 000 psi then 10 000 psi over 10 pre-milling cycles each, then at 20 000 psi over 20 milling cycles. A heat exchanger was connected to the homogenizing valve and maintained at −15° C. using an F32-MA cooling circulator (Julabo GmbH, Seelbach, Germany). An aliquot was removed from the suspension at the end of the process to measure the particle size distribution (PSD) of cisplatin microcrystals by laser diffraction (see below).

Then, castor oil hydrogenated (BASF, Ludwigshafen, Germany) and TPGS (Sigma-Aldrich, St-Louis, USA) solubilized in heated isopropanol were added to the microcrystal suspension to obtain a final concentration of 1.0% w/v of cisplatin and 1.0% w/v of castor oil hydrogenated/TPGS (99:1 w/w) mixture and spray dried with a Mini-Spray Dryer B-290 (Büchi Labortechnik AG, Flawil, Switzerland) to obtain a DPI formulation for human use. The operating parameters used during spray-drying were as follows: feed rate 3.0 g/min, inlet temperature 70° C., 0.7 mm nozzle, 1.5 mm nozzle-cap, compressed air at 800 L/min and drying air flow 35 m$^3$/h. The apparatus was equipped with a B-296 dehumidifier (Büchi Labortechnik AG) to maintain the relative humidity at 50% HR during spray-drying.

The geometrical PSD of bulk cisplatin, cisplatin microparticles from the size-reduction process, and cisplatin dry powder formulation, was measured as suspended and individualized particles. This was done using a Mastersizer 3000 laser diffractometer (Malvern Instruments Ltd., Worcestershire, UK) connected to a Hydro MV dispenser equipped with a 40 W ultrasonic probe (Malvern Instruments Ltd.) as described in the Example 1.

Example 3.—Analysis of Deposition Rate of Cisplatin Dry Powder Formulations Prepared According to Examples 1 and 2

Formulations according to the comparative example (Composition F5 in Levet al) and according to examples 1 and 2 have been analyzed regarding their fine particle fraction values.

The fine particle fraction (FPF)—which is the percentage related to the recovered dose of cisplatin-based particles with an aerodynamic diameter (dae) below 5 μm—and the aerodynamic PSD, characterized by the mass median aerodynamic diameter (MMAD), were determined using an MsLI (Copley Scientific, Nottingham, UK) —Apparatus C—as described in the European Pharmacopoeia 8.0. (2014). A mass of 20 mg of each DPI formulation (comparative example and according to example 2), previously sieved through a 355 mm stainless steel mesh, was weighed in a size 3 HPMC capsule (Quali-V-1, Qualicaps, Madrid, Spain) and deposited in the MsLI using RS.01 dry powder inhaler (RPC Plastiape, Osnago, Italy) mounted on the inhalation port with its adapter (n=3).

A deposition flow rate of 100±5 L/min measured using a DFM3 flow meter (Copley Scientific, Nottingham, UK) was obtained with two HCP5 air pumps (Copley Scientific, Nottingham, UK) connected in series to a TPK critical flow controller (Copley Scientific, Nottingham, UK).

At this flow rate, cut-off diameters were 10.0, 5.3, 2.4, 1.3 and 0.4 mm between each stage of the MsLI. The microorifice collector (MOC) filter (i.e. stage 5) contained a Fluoropore 9 cm PTFE membrane with 0.45 mm pore size bonded on a high-density polyethylene support (Merck Millipore, Darmstadt, Germany). The critical flow controller was used to ensure a deposition time of 2.4 s at 100 L/min and a critical flow with a P3/P2 ratio<0.5, as required by the European Pharmacopoeia 8.0. (2014).

After impaction, the four upper stages of the MsLI were given a first rinse using 20 mL of previously filled 0.5% w/v Poloxamer 407 in ultrapure water/isopropanol (60:40 v/v) as the dilution phase, a second rinse using 25 mL of DMF and a third rinse using dilution phase, adjusted to 100.0 mL and ultrasonicated for 30 min. Drug deposition in the capsule, in the device, in the induction port and on the MOC filter were determined after solubilization with 100.0 mL of dilution phase and ultrasonication for 30 min. The impacted mass in each stage was determined by quantification of the cisplatin content by the validated electrothermal atomic absorption spectrometry (ETAAS) method described by Levet el al (Levet, Int J Pharm 2016).

Results were then plotted in Copley Inhaler Testing Data Analysis Software1 (Copley Scientific, Nottingham, UK) to obtain the FPD below 5 μm. This was done from interpolation of the recovered mass vs. the cut-off diameter of the corresponding stage. The FPF was expressed as a percentage of the nominal dose.

FIG. 1 presents the FPF values (%) of the comparative example (Composition F5 in Levet al) and examples 1 and 2 (mean±SD, n=2-3), demonstrating the superiority the cisplatin compositions disclosed in the present disclosure, compared to other triglyceride-based cisplatin DPI formulations in terms of pulmonary deposition Example 4.—Analysis of Dissolution Rate of Cisplatin from Cisplatin Dry Powder Formulations Prepared According to Examples 1 and 2

Dissolution properties of DPI formulations were established by applying a method described by Levet et al (Levet et al, Int J Pharm 2016). This method derived from the paddle over disk method from USP39 using a modified dissolution apparatus type V for transdermal patches. The release profile of cisplatin was determined from the whole respirable fraction (dae smaller or equal to 5 μm) of the DPI formulation, selected using a Fast Screening Impactor (FSI, Copley Scientific, Nottingham, UK). An appropriate mass of each DPI formulation, equivalent to a deposited dose of 3 mg of cisplatin was weighed into a size 3 HPMC capsule (Quali-V-I Qualicaps, Madrid, Spain). This was then deposited using an RS.01 DPI device (RPC Plastiape) onto a Fluoropore® hydrophobic PTFE membrane filter with 0.45 mm pore size (Merck Millipore, Darmstadt, Germany), with the FSI (2.4 s, 100 L/min) equipped with the corresponding pre-separator insert. The Fluoropore filter, with the deposited powder facing up, was then covered with an Isopore® 0.4 mm hydrophilic polycarbonate filter (Merck-Milipore, Germany) and fixed onto a watchglass-PTFE disk assembly (Copley, Nottingham, UK) with the clips and PTFE mesh screen provided. The disk assembly was then submerged in a dissolution vessel of an AT7 dissolution apparatus (Sotax AG, Aesch, Switzerland) with 400 mL of modified simulated lung fluid (mSLF) (Son and McConville, 2009)—a medium that mimics the lungs electrolytic and surfactant composition.

Dissolution testing was realized in accordance with sink conditions, at 37±0.2° C., pH 7.35±0.05. Paddles, set at 25±2 mm between the blade and the center of the disk-assembly, were set at a rotating speed of 50±4 rpm. Sampling volumes of 2.0 mL were filtered through 0.22 mm pore size cellulose acetate syringe filters (VWR, Leuven, Belgium) at pre-established times between 2 min and 24 h, and replaced with 2.0 mL of free pre-heated mSLF.

At the end of the dissolution assay, the disk assembly was opened into the dissolution vessel and ultrasonicated for 30 min to establish the 100% cisplatin dissolution value.

Figure 2:
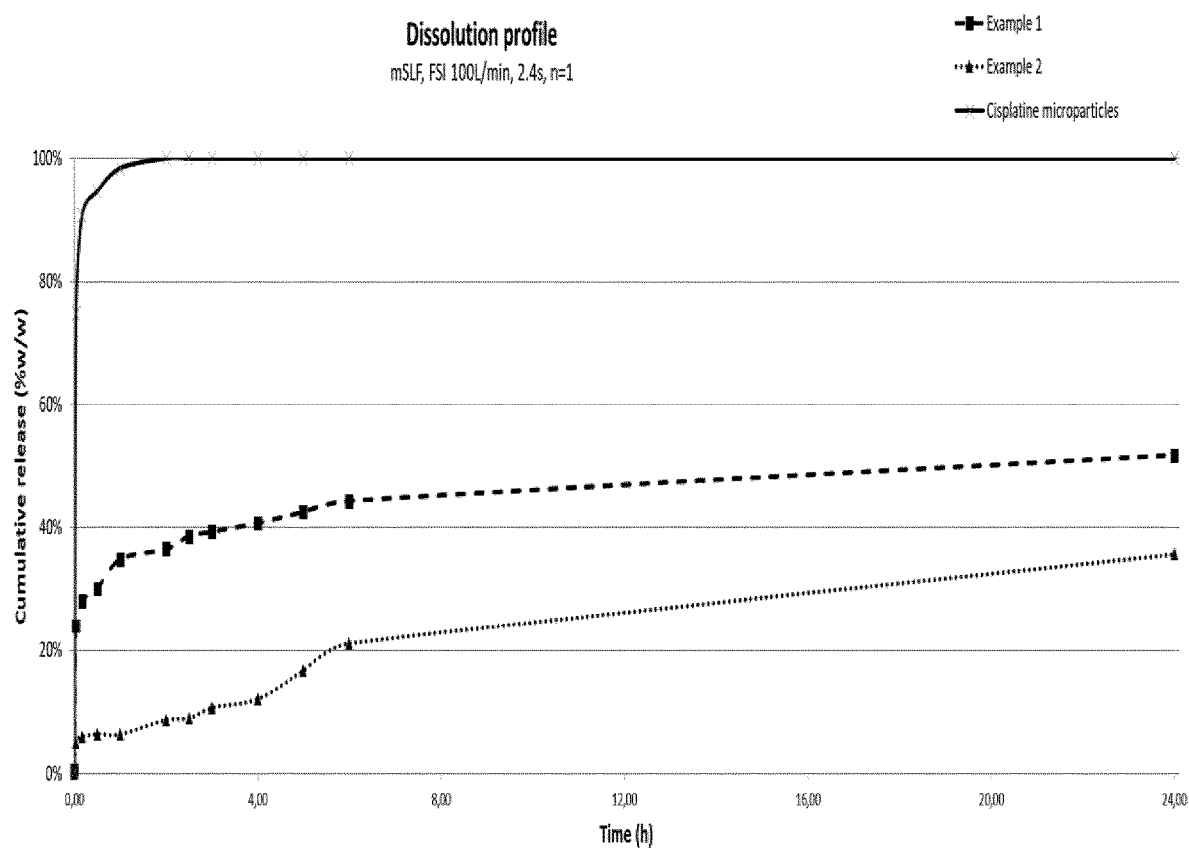
FIG. 2 presents the release profiles of cisplatin from the respirable fraction of the DPI formulations prepared according to Examples 1 and 2, compared to the comparative formulation composed of cisplatin microparticles only.

FIG. 2 presents the release profiles of cisplatin from the respirable fraction of the DPI formulations prepared according to Examples 1 and 2, compared to the comparative formulation composed of cisplatin microparticles only.

Example 5.—Preparation of Insulin Dry Powder Formulation n° 1

Insulin was first suspended in isopropanol (2% w/v), and dispersion of the powder was ensured by 10 min of ultrasonication in a 40 kHz Branson 2510 bath. The particle size was then reduced using an EmulsiFlex-C5 high-pressure homogenizer (Aves-tin Inc., Ottawa, Canada). Pre-milling low-pressure homogenization cycles were first conducted on the insulin suspension to further decrease the particle size (10 cycles at 7000 PSI and 10 cycles at 12,000 PSI). HPH was then finally applied for 30 cycles at 24,000 PSI. These cycles were conducted by recirculating the processed suspension directly into the sample tank (closed loop). Because HPH causes a sample temperature increase (increase of 30° C. following 20 cycles at 24,000 PSI), all operations were carried out using a heat exchanger placed ahead of the homogenizing valve, with the sample temperature maintained at 5±1° C.

An aliquot was removed from the suspension at the end of the process to measure the particle size distribution (PSD) of insulin microcrystals by laser diffraction (see below).

Then, castor oil hydrogenated (BASF, Ludwigshafen, Germany) and TPGS (Sigma-Aldrich, St-Louis, USA) solubilized in heated isopropanol were added to the microcrystal suspension to obtain a final concentration of 1.0% w/v of insulin and 1.0% w/v of castor oil hydrogenated/TPGS (99:1 w/w) mixture and spray dried with a Mini-Spray Dryer B-290 (Büchi Labortechnik AG, Flawil, Switzerland) to obtain a DPI formulation for human use. The operating parameters used during spray-drying were as follows: feed rate 3.0 g/min, inlet temperature 70° C., 0.7 mm nozzle, 1.5 mm nozzle-cap, compressed air at 800 L/min and drying air flow 35 m$^3$/h. The apparatus was equipped with a B-296 dehumidifier (Büchi Labortechnik AG) to maintain the relative humidity at 50% HR during spray-drying.

The geometrical PSD of bulk insulin, insulin microparticles from the size-reduction process, and insulin dry powder formulation, was measured as suspended and individualized particles and was within the range of the present disclosure. This was done using a Mastersizer 3000 laser diffractometer (Malvern Instruments Ltd., Worcestershire, UK) connected to a Hydro MV dispenser equipped with a 40 W ultrasonic probe (Malvern Instruments Ltd.) as described in the Example 1.

Example 6. —Preparation of Insulin Dry Powder Formulation n° 2

Insulin was first suspended in isopropanol (2% w/v), and dispersion of the powder was ensured by 10 min of ultrasonication in a 40 kHz Branson 2510 bath. The particle size was then reduced using an EmulsiFlex-C5 high-pressure homogenizer (Aves-tin Inc., Ottawa, Canada). Pre-milling low-pressure homogenization cycles were first conducted on the insulin suspension to further decrease the particle size (10 cycles at 7000 PSI and 10 cycles at 12,000 PSI). HPH was then finally applied for 30 cycles at 24,000 PSI. These cycles were conducted by recirculating the processed suspension directly into the sample tank (closed loop). Because HPH causes a sample temperature increase (increase of 30° C. following 20 cycles at 24,000 PSI), all operations were carried out using a heat exchanger placed ahead of the homogenizing valve, with the sample temperature maintained at 5±1° C.

An aliquot was removed from the suspension at the end of the process to measure the particle size distribution (PSD) of insulin microcrystals by laser diffraction (see below).

Then, castor oil hydrogenated (BASF, Ludwigshafen, Germany) and TPGS (Sigma-Aldrich, St-Louis, USA) solubilized in heated isopropanol were added to the microcrystal suspension to obtain a final concentration of 1.5% w/v of insulin and 0.5% w/v of castor oil hydrogenated/TPGS (99:1 w/w) mixture and spray dried with a Mini-Spray Dryer B-290 (Büchi Labortechnik AG, Flawil, Switzerland) to obtain a DPI formulation for human use. The operating parameters used during spray-drying were as follows: feed rate 3.0 g/min, inlet temperature 70° C., 0.7 mm nozzle, 1.5 mm nozzle-cap, compressed air at 800 L/min and drying air flow 35 m$^3$/h. The apparatus was equipped with a B-296 dehumidifier (Büchi Labortechnik AG) to maintain the relative humidity at 50% HR during spray-drying.

The geometrical PSD of bulk insulin, insulin microparticles from the size-reduction process, and insulin dry powder formulation, was measured as suspended and individualized particles and was within the range of the present disclosure. This was done using a Mastersizer 3000 laser diffractometer (Malvern Instruments Ltd., Worcestershire, UK) connected to a Hydro MV dispenser equipped with a 40 W ultrasonic probe (Malvern Instruments Ltd.) as described in the Example 1.

Example 7. —Preparation of Budesonide Dry Powder Formulation for Inhalation n° 1

Budesonide (1% w/v) was first solubilized in isopropanol under magnetic stirring. Then, castor oil hydrogenated (BASF, Ludwigshafen, Germany) and TPGS (Sigma-Aldrich, St-Louis, USA) solubilized in heated isopropanol were added to the microcrystal suspension to obtain a final concentration of 1.0% w/v of budesonide and 1.0% w/v of castor oil hydrogenated/TPGS (99:1 w/w) mixture and spray dried with a Mini-Spray Dryer B-290 (Büchi Labortechnik AG, Flawil, Switzerland) to obtain a DPI formulation for human use. The operating parameters used during spray-drying were as follows: feed rate 3.0 g/min, inlet temperature 70° C., 0.7 mm nozzle, 1.5 mm nozzle-cap, compressed air at 800 L/min and drying air flow 35 m$^3$/h. The apparatus was equipped with a B-296 dehumidifier (Büchi Labortechnik AG) to maintain the relative humidity at 50% HR during spray-drying.

The geometrical PSD of bulk budesonide dry powder formulation was measured as suspended and individualized particles and was within the range of the present disclosure. This was done using a Mastersizer 3000 laser diffractometer (Malvern Instruments Ltd., Worcestershire, UK) connected to a Hydro MV dispenser equipped with a 40 W ultrasonic probe (Malvern Instruments Ltd.) as described in the Example 1.

Example 8.—Preparation of Budesonide Dry Powder Formulation for Inhalation n° 2

Budesonide (1.5% w/v) was first solubilized in isopropanol under magnetic stirring. Then, castor oil hydrogenated (BASF, Ludwigshafen, Germany) and TPGS (Sigma-Aldrich, St-Louis, USA) solubilized in heated isopropanol were added to the microcrystal suspension to obtain a final concentration of 1.5% w/v of budesonide and 0.5% w/v of castor oil hydrogenated/TPGS (99:1 w/w) mixture and spray dried with a Mini-Spray Dryer B-290 (Büchi Labortechnik AG, Flawil, Switzerland) to obtain a DPI formulation for human use. The operating parameters used during spray-drying were as follows: feed rate 3.0 g/min, inlet temperature 70° C., 0.7 mm nozzle, 1.5 mm nozzle-cap, compressed air at 800 L/min and drying air flow 35 m$^3$/h. The apparatus was equipped with a B-296 dehumidifier (Büchi Labortechnik AG) to maintain the relative humidity at 50% HR during spray-drying.

The geometrical PSD of bulk budesonide dry powder formulation was measured as suspended and individualized particles and was within the range of the present disclosure. This was done using a Mastersizer 3000 laser diffractometer (Malvern Instruments Ltd., Worcestershire, UK) connected to a Hydro MV dispenser equipped with a 40 W ultrasonic probe (Malvern Instruments Ltd.) as described in the Example 1.

Examples 9. Preparation of Budesonide Dry Powder Formulation n° 3

An amount of 10 g of micronized budesonide, 9.9 g castor oil hydrogenated and 0.1 g TPGS were blended to homogeneity in a Turbula® mixer (Willy A. Bachofen AG, Muttenz, Switzerland). The homogenous blend was then extruded though a twin-screw extruder (Process-11, Thermo Fischer Scientific, Massachusetts, USA) at an appropriated temperature to obtain a homogeneous lipid matrix. The extrudate was then cut to obtain coarse pellets and the pellets were placed in an incubator at an appropriate storage condition to transform the lipid matrix in a stable polymorphic. The pellets were finally milled by means of a jet-mill (at appropriate pellets feeding rate, injection pressure and grinding pressure) to obtain microparticles for inhalation (DPI) for human use.

Example 10.—Preparation of Pemetrexed Dry Powder Formulation for Inhalation n° 1

Briefly, raw pemetrexed disodium (heptahydrate form) microcrystals from bulk powder (Carbosynth Limited, Berkshire, United Kingdom) were first suspended in 50 mL isopropanol to reach a concentration of 1% w/v in the presence of 0.05% w/v TPGS (Sigma-Aldrich, St-Louis, USA) and reduced in size by high-speed (10 min at 24 000 rpm) (X620 motor and a T10 dispersing shaft, IngenieurbOro CAT M. Zipperer GmbH, Staufen, Germany) and high-pressure homogenization (EmulsiFlex-C3 high-pressure homogenizer, Avestin Inc., Ottawa, Canada) at 25 000 psi over 20 milling cycles. A heat exchanger was connected to the homogenizing valve and maintained at +5° C. using an F32-MA cooling circulator (Julabo GmbH, Seelbach, Germany). An aliquot was removed from the suspension at the end of the process to measure the particle size distribution (PSD) of pemetrexed microcrystals by laser diffraction (see below).

Then, 1% w/v castor oil hydrogenated (BASF, Ludwigshafen, Germany) were solubilized in the heated (50° C.) microcrystal suspension suspension and spray dried with a Mini-Spray Dryer B-290 (Büchi Labortechnik AG, Flawil, Switzerland) to obtain a DPI formulation for human use. The operating parameters used during spray-drying were as follows: feed rate 3.0 g/min, inlet temperature 70° C., 0.7 mm nozzle, 1.5 mm nozzle-cap, compressed air at 800 L/min and drying air flow 35 m$^3$/h. The apparatus was equipped with a B-296 dehumidifier (Büchi Labortechnik AG) to maintain the relative humidity at 50% HR during spray-drying.

The geometrical PSD of bulk pemetrexed, pemetrexed microparticles from the size-reduction process, and pemetrexed dry powder formulation, was measured as suspended and individualized particles and was within the range of the present disclosure. This was done using a Mastersizer 3000 laser diffractometer (Malvern Instruments Ltd., Worcestershire, UK) connected to a Hydro MV dispenser equipped with a 40 W ultrasonic probe (Malvern Instruments Ltd.) as described in the Example 1.

Example 11.—Analysis of Deposition Rate of the Pemetrexed Dry Powder Formulation Prepared According to Example 10

The formulation according to examples 10 has been analyzed regarding its in vitro pulmonary deposition pattern and FPF value.

The FPF—which is the percentage related to the recovered dose of pemetrexed-based particles with an aerodynamic diameter (dae) below 5 μm—and the aerodynamic PSD, characterized by the MMAD, were determined using a NGI (Copley Scientific, Nottingham, UK)—Apparatus E—as described in the European Pharmacopoeia 8.0. (2014). A mass of 20 mg of the DPI formulation (according to example 10 and the comparative formulation composed of pemetrexed microparticles only), previously sieved through a 355 mm stainless steel mesh, was weighed in a size 3 HPMC capsule (Quali-V-L, Qualicaps, Madrid, Spain) and deposited in the NGI using RS.01 dry powder inhaler (RPC Plastiape, Osnago, Italy) mounted on the inhalation port with its adapter (n=3).

A deposition flow rate of 100±5 L/min measured using a DFM3 flow meter (Copley Scientific, Nottingham, UK) was obtained with two HCP5 air pumps (Copley Scientific, Nottingham, UK) connected in series to a TPK critical flow controller (Copley Scientific, Nottingham, UK).

At this flow rate, cut-off diameters were 6.12, 3.42, 2.18, 1.31, 0.72, 0.40 and 0.24 μm between each stage of the NGI. The critical flow controller was used to ensure a deposition time of 2.4 s at 100 L/min and a critical flow with a P3/P2 ratio<0.5, as required by the European Pharmacopoeia 8.0 (2014).

After impaction, the pemetrexed mass deposited in the capsule, in the device, in the induction port, in the pre-separator, in the 7 stages and in the MOC of the NGI were collected with a ultrapure water/DMF (30:70 v/v) as the dilution phase and ultrasonicated for 30 min. The impacted mass in each stage was determined by quantification of the pemetrexed content by a validated HPLC. The chromatographic system (HP 1200 series, Agilent Technologies, Diegem, Belgium) was equipped with a quaternary pump, an auto sampler, and a diode array detector. The separations were performed on a reverse-phase Hypersil Gold C18 column (5 mm, 250 mm×4.6 mm) (Thermo Fisher Scientific, Waltham, USA). The mobile phase consisted of ultrapure water/acetonitrile (86:14) acidified with 0.4% formic acid, which was delivered at a flow rate of 1 mL/min. The quantification was performed at 256 nm. The volume injected was 20 μL, the temperature was set at 30° C., and the analysis run time was 15 min.

Results were then plotted in Copley Inhaler Testing Data Analysis Software1 (Copley Scientific, Nottingham, UK) to obtain the FPD below 5 μm. This was done from interpolation of the recovered mass vs. the cut-off diameter of the corresponding stage. The FPF was expressed as a percentage of the nominal dose.

Figure 3:
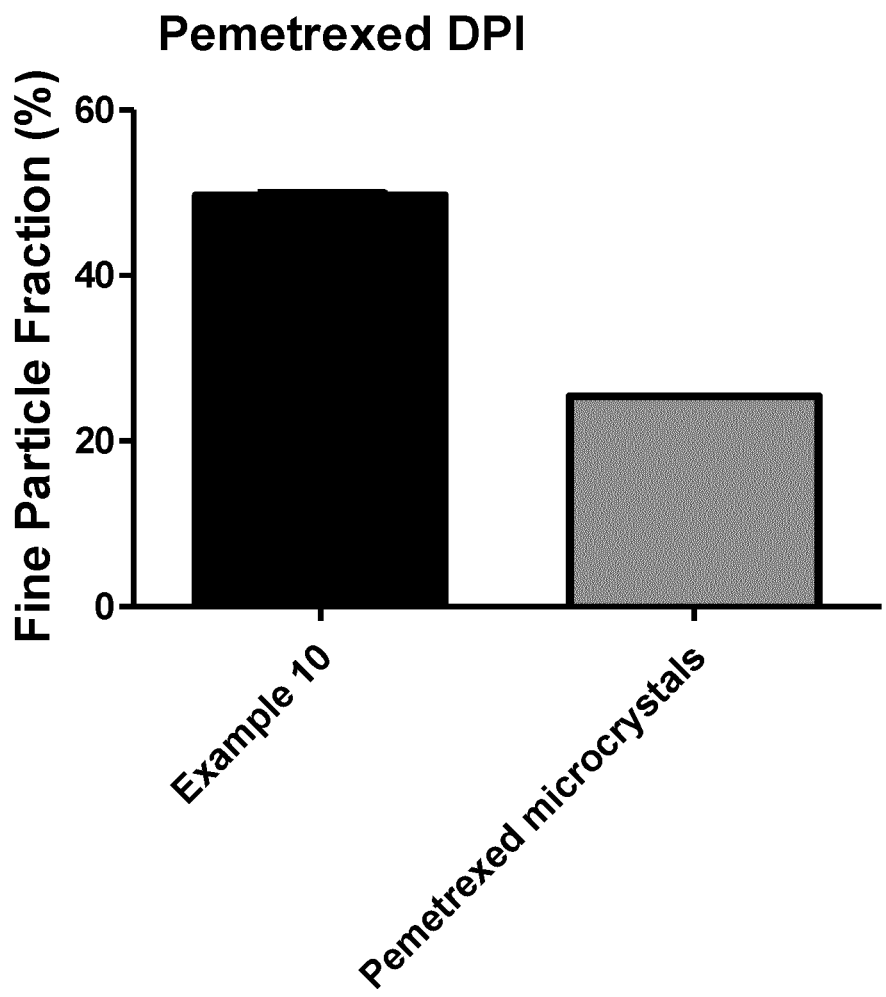
FIG. 3 presents the FPF value of Example 10, compared to the comparative formulation composed of pemetrexed microparticles only (mean±SD, n=3 and 1, respectively), demonstrating the superiority of Example 10 to a conventional DPI formulation in terms of pulmonary deposition.

FIG. 3 presents the FPF value of Example 10, compared to the comparative formulation composed of pemetrexed microparticles only (mean±SD, n=3 and 1, respectively), demonstrating the superiority of Example 10 to a conventional DPI formulation in terms of pulmonary deposition.

Example 12.—Analysis of Dissolution Rate of Pemetrexed from the Pemetrexed Dry Powder Formulation Prepared According to Examples 10

Dissolution properties of the DPI formulation was established by applying an adaptation of the method described by Pilcer et al (Pilcer et al, J Pharm Sci 2013). A dissolution system (Copley Scientific, Nottingham, UK) specifically developed for DPI release profile studies was used with a method adapted from the "Paddle over Disc" (Eur.Ph. 7). To study the release profiles of the particles which deposit in the lungs, a fractionation of the pemetrexed formulation was first performed with an NGI. The cup at stage 3 was chosen to be equipped with a removable disc insert to collect particles. Of particular interest, at the selected inhalation rate (100 L/min for 2.4 s), the cut-off diameters of stage 3 ranged between 2.18 and 3.42 μm, allowing the selection of particles targeting the lung. Capsules with an appropriate amount of formulation according to Example 10 were weighted to collect about 6 mg pemetrexed in the stage 3. Then, the disc insert was covered with a polycarbonate membrane (0.4 μm pore size) (Merck Millipore) and put into a paddle dissolution apparatus (Erweka DT6; ERWEKA GmbH, Heusenstamm, Hesse, Germany) filled with 400 mL of mSLF (Son and McConville, 2009)—a medium that mimics the lungs electrolytic and surfactant composition.

Dissolution testing was realized in accordance with sink conditions, at 37±0.2° C., pH 7.35±0.05. Paddles, set at 25±2 mm between the blade and the center of the disk-assembly, were set at a rotating speed of 50±4 rpm. Sampling volumes of 2.0 mL were filtered through 0.22 mm pore size cellulose acetate syringe filters (VWR, Leuven, Belgium) at pre-established times between 2 min and 24 h, and replaced with 2.0 mL of free pre-heated mSLF.

At the end of the dissolution assay, the disk assembly was opened into the dissolution vessel and ultrasonicated for 30 min to establish the 100% pemetrexed dissolution value.

Figure 4:
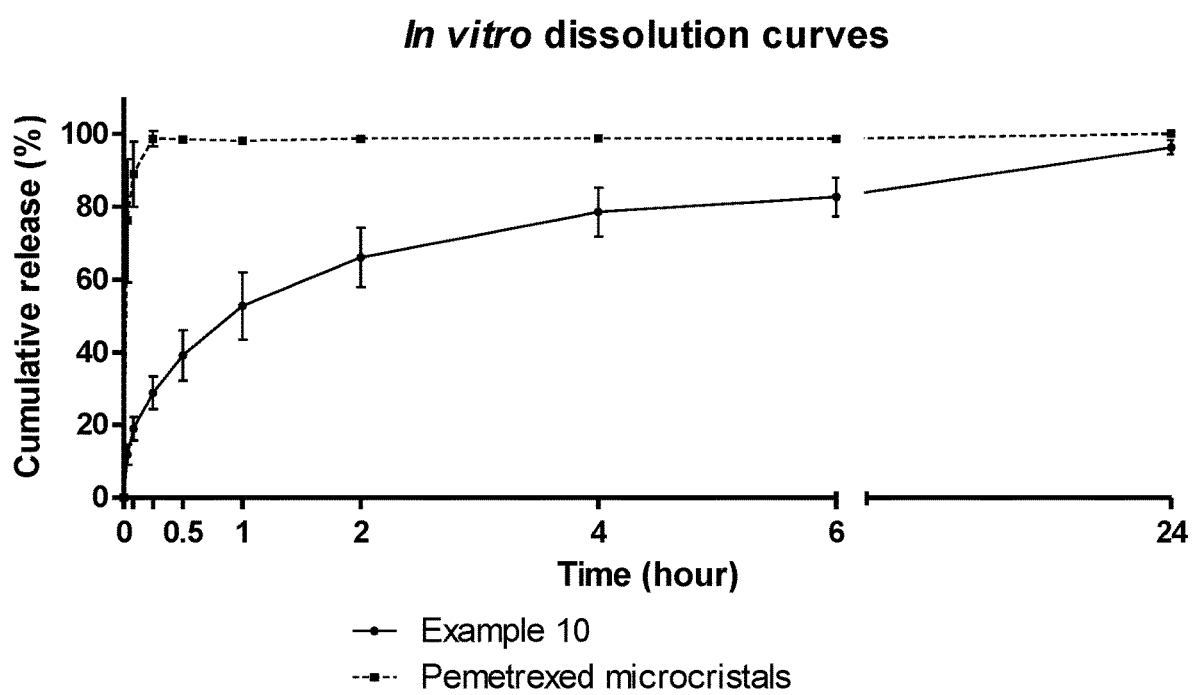
FIG. 4 presents the release profiles of pemetrexed from the respirable fraction of the DPI formulation prepared according to Example 10, compared to the comparative formulation composed of pemetrexed microparticles only (mean±SD, n=3).

FIG. 4 presents the release profiles of pemetrexed from the respirable fraction of the DPI formulation prepared according to Example 10, compared to the comparative formulation composed of pemetrexed microparticles only (mean±SD, n=3).

The similarity factor f2 was used to compare the two dissolution profiles (Shah et al, Pharm Res 1998). The curves were significantly different (f2<50). Moreover, the cumulative release values at all the timepoints from Example 10 were significantly lower compared to those from pemetrexed microcrystals (p<0.05, t-test), e.g. at 1 h, respectively, 53±9% vs 97.9±0.9% (p<0.01), indicating a controlled release profile of pemetrexed from a composition of the present disclosure.

Example 13. —Preparation of Insulin Dry Powder Formulation n° 3

Insulin (Sigma-Aldrich) was first suspended in isopropanol (1% w/v) using magnetic stirring and dispersion of the powder was ensured by 10 min of ultrasonication in a 40 kHz Branson 2510 bath. The particle size was then reduced using an EmulsiFlex-C3 high-pressure homogenizer (Avestin Inc., Ottawa, Canada) for 30 cycles at 22,000 PSI. These cycles were conducted by recirculating the processed suspension directly into the sample tank (closed loop). Because HPH causes a sample temperature increase, all operations were carried out using a heat exchanger placed ahead of the homogenizing valve, with the sample temperature maintained at 5±1° C.

An aliquot was removed from the suspension at the end of the process to measure the particle size distribution (PSD) of insulin microcrystals by laser diffraction (see below).

Then, 1% w/v castor oil hydrogenated (BASF, Ludwigshafen, Germany) were solubilized in the heated (50° C.) microcrystal suspension suspension and spray dried with a Mini-Spray Dryer B-290 (Büchi Labortechnik AG, Flawil, Switzerland) to obtain a DPI formulation for human use. The operating parameters used during spray-drying were as follows: feed rate 3.0 g/min, inlet temperature 70° C., 0.7 mm nozzle, 1.5 mm nozzle-cap, compressed air at 800 L/min and drying air flow 35 m$^3$/h. The apparatus was equipped with a B-296 dehumidifier (Büchi Labortechnik AG) to maintain the relative humidity at 50% HR during spray-drying.

The geometrical PSD of bulk insulin, insulin microparticles from the size-reduction process, and insulin dry powder formulation, was measured as suspended and individualized particles and was within the range of the present disclosure. This was done using a Mastersizer 3000 laser diffractometer (Malvern Instruments Ltd., Worcestershire, UK) connected to a Hydro MV dispenser equipped with a 40 W ultrasonic probe (Malvern Instruments Ltd.) as described in the Example 1.

Example 14.—Analysis of Deposition Rate of the Insulin Dry Powder Formulations Prepared According to Example 13

The formulation according to example 13 has been analyzed regarding their FPF value.

The FPF—which is the percentage related to the recovered dose of insulin-based particles with an dae below 5 μm—was determined using a Fast Screening Impactor (FSI) (Copley Scientific, Nottingham, UK). The FSI employs a two-stage separation process in which first large non-inhalable boluses are captured in a liquid trap followed by a fine-cut impaction stage at 5 microns (i.e. corresponding to FPF). A mass of 10 mg of the DPI formulations (according to example 13), previously sieved through a 355 mm stainless steel mesh, was weighed in a size 3 HPMC capsule (Quali-V-1, Qualicaps, Madrid, Spain) and deposited in the FSI using RS.01 dry powder inhaler (RPC Plastiape, Osnago, Italy) mounted on the inhalation port with its adapter (n=3).

A deposition flow rate of 100±5 L/min measured using a DFM3 flow meter (Copley Scientific, Nottingham, UK) was obtained with two HCP5 air pumps (Copley Scientific, Nottingham, UK) connected in series to a TPK critical flow controller (Copley Scientific, Nottingham, UK). The critical flow controller was used to ensure a deposition time of 2.4 s at 100 L/min.

After impaction, the insulin mass deposited in the capsule, in the device, in the induction port, in the pre-separator and onto the a Fluoropore 9 cm PTFE membrane with 0.45 mm pore size bonded on a high-density polyethylene support (Merck Millipore, Darmstadt, Germany), were collected with 0.01 M HCl as the dilution phase and ultrasonicated for 30 min. The impacted mass in each stage was determined by quantification of the insulin content by the HPLC method described in the European Pharmacopoeia 9.2. (2017). The FPF was expressed as a percentage of the nominal dose.

Figure 5:
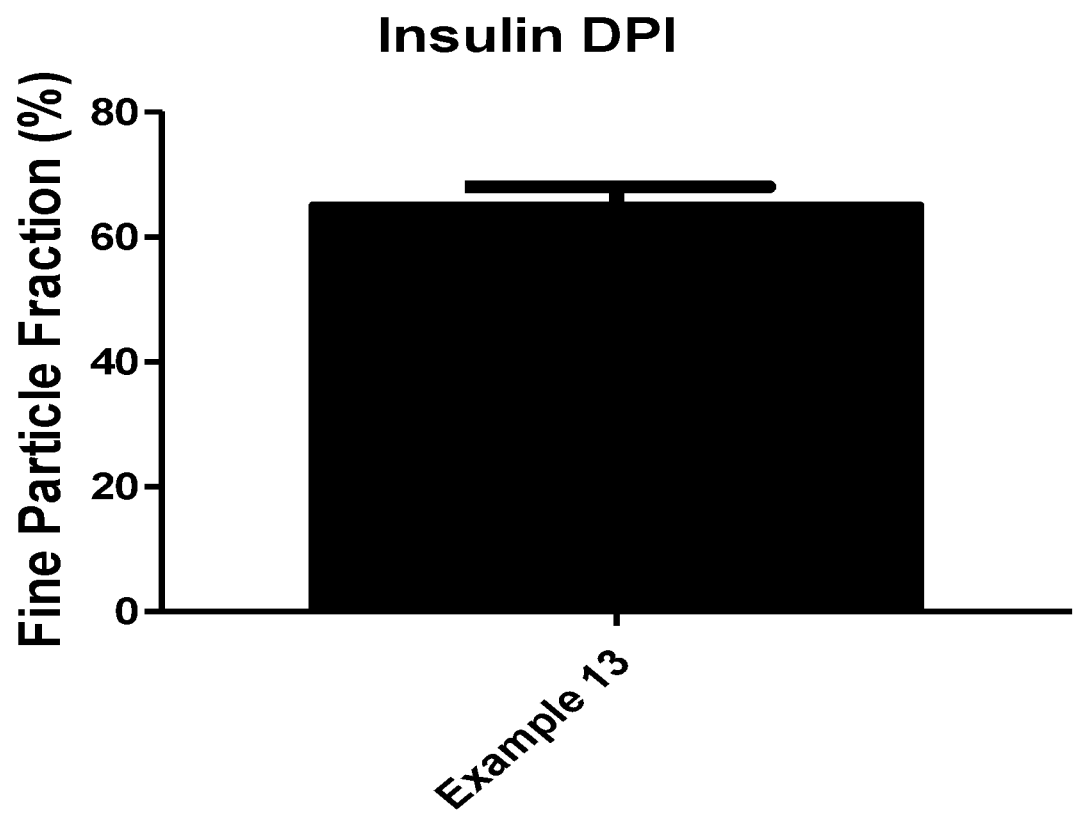
FIG. 5 presents the FPF values of Example 13 (mean±SD), demonstrating high pulmonary deposition rate of insulin-based DPI composition disclosed in the present disclosure.

FIG. 5 presents the FPF values of Example 13 (mean±SD), demonstrating high pulmonary deposition rate of insulin-based DPI composition disclosed in the present disclosure.

Example 15.—Analysis of Dissolution Rate of Insulin from the Insulin Dry Powder Formulations Prepared According to Example 13

Dissolution properties of the DPI formulations according to Example 13 was established by applying an adaptation of the method described by Depreter et al (Depreter et al, Eur J Pharm Biopharm 2012). A dissolution system (Copley Scientific, Nottingham, UK) specifically developed for DPI release profile studies was used with a method adapted from the "Paddle over Disc" (Eur.Ph. 7). To study the release profiles of the particles which deposit in the lungs, a fractionation of the insulin formulation was first performed with an NGI. The cup at stage 3 was chosen to be equipped with a removable disc insert to collect particles. Of particular interest, at the selected inhalation rate (100 L/min for 2.4 s), the cut-off diameters of stage 3 ranged between 2.18 and 3.42 µm, allowing the selection of particles targeting the lung. Capsules with an appropriate amount of formulation according to Example 13 were weighted to collect about 3 mg insulin in the stage 3. Then, the disc insert was covered with a polycarbonate membrane (0.4 µm pore size) (Merck Millipore) and put into a paddle dissolution apparatus (Erweka DT6; ERWEKA GmbH, Heusenstamm, Hesse, Germany) filled with 400 mL of 0.01 mM phosphate buffer saline (PBS) at pH 7.4.

Dissolution testing was realized in accordance with sink conditions, at 37±0.2° C., pH 7.35±0.05. Paddles, set at 25±2 mm between the blade and the center of the disk-assembly, were set at a rotating speed of 50±4 rpm. Volumes of 5.0 mL were sampled at pre-established times between 2 min and 24 h, and replaced with 5.0 mL of free pre-heated PBS.

At the end of the dissolution assay, the disk assembly was opened into the dissolution vessel and ultrasonicated for 30 min to establish the 100% insulin dissolution value.

The samples were lyophilized (Christ Epsilon 1-6) in the presence of 3% w/v trehalose. Lyophilisates were dissolved in 500 µL HCl 0.02N and injected in the HPLC system using the method described in the European Pharmacopoeia 9.2. (2017).

Figure 6:
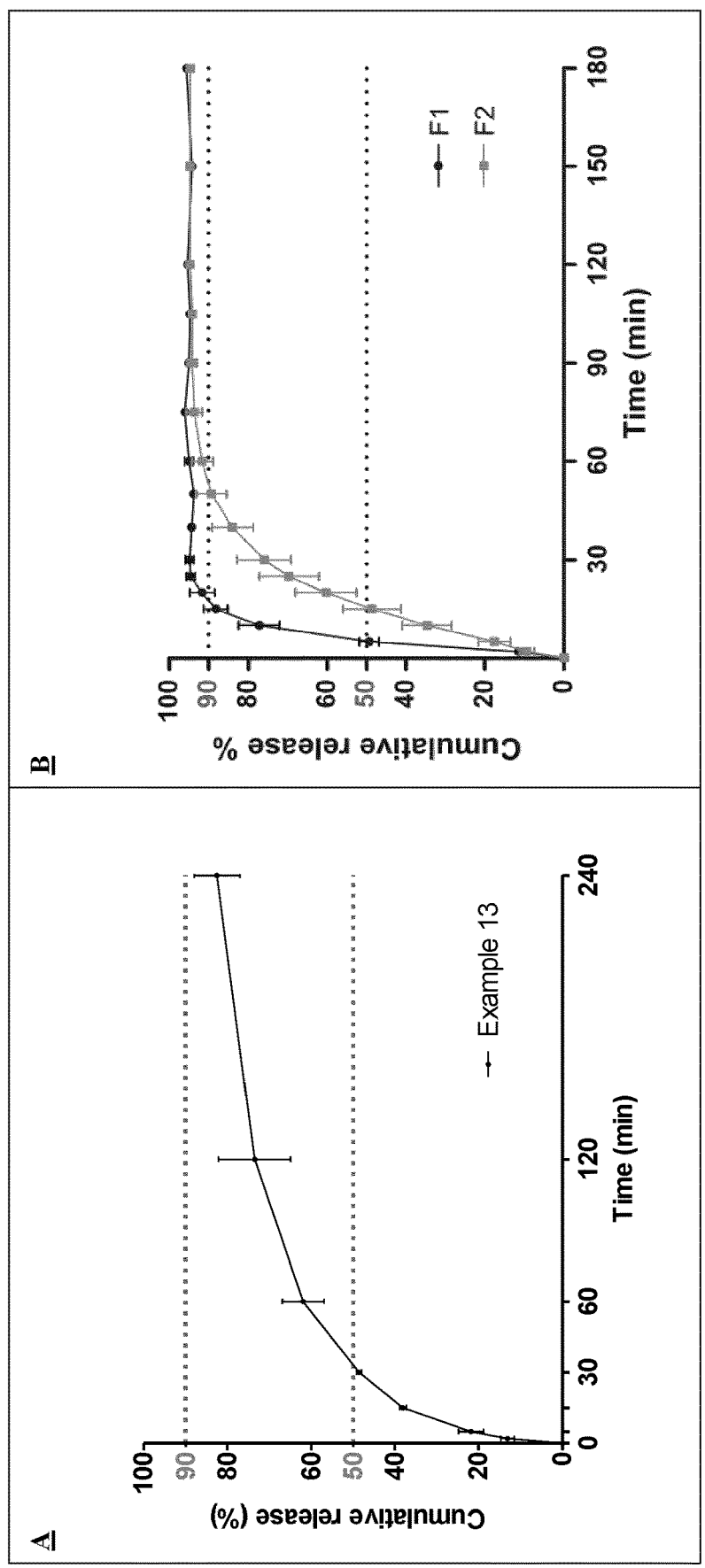
FIG. 6 presents the release profiles of insulin from the respirable fraction of the DPI formulations prepared according to Example 13 (to up to 240 min, mean±SD, n=2) (A), compared to the comparative formulations described by Depreter et al (to up to 180 min) (B).

FIG. 6 presents the release profiles of insulin from the respirable fraction of the DPI formulations prepared according to Example 13 (to up to 240 min, mean±SD, n=2) (A), compared to the comparative formulations described by Depreter et al (to up to 180 min) (B).

The cumulative release values at different timepoints from Example 13 were lower compared to those from the two formulations from Depreter et al, e.g. at 1 h, respectively, about 60% vs about 100%, demonstrating the superiority of the insulin compositions disclosed in the disclosure in terms of controlling the insulin release, on both insulin microcrystals and lipid-coated insulin microcrystals described by Depreter et al (respectively F1 and F2 in FIG. 6).

Example 16. —Preparation of Cisplatin Dry Powder Formulation n° 3 and a Comparative Example Cisplatin (Umicore, Hanau-Wolfgang, Germany) was first suspended in 50 mL ethanol to reach a concentration of 5% w/v and reduced in size by high-speed (10 min at 24 000 rpm) (X620 motor and a T10 dispersing shaft, IngenieurbOro CAT M. Zipperer GmbH, Staufen, Germany) and high-pressure homogenization using an EmulsiFlex-C3 high-pressure homogenizer (Avestin Inc., Ottawa, Canada) for 40 cycles at 20,000 PSI. These cycles were conducted by recirculating the processed suspension directly into the sample tank (closed loop). Because HPH causes a sample temperature increase, all operations were carried out using a heat exchanger placed ahead of the homogenizing valve, with the sample temperature maintained at 15±1° C.

An aliquot was removed from the suspension at the end of the process to measure the PSD of cisplatin microcrystals by laser diffraction (see below).

Then, castor oil hydrogenated (BASF, Ludwigshafen, Germany) and TPGS (Sigma-Aldrich, St-Louis, USA) (or tristearin for the comparative example) solubilized in heated isopropanol were added to the microcrystal suspension to obtain a final concentration of 2.0% w/v of cisplatin and 2.0% w/v of triglyceride/TPGS (99:1 w/w) mixture and spray dried with a Mini-Spray Dryer B-290 (Büchi Labortechnik AG, Flawil, Switzerland) to obtain a DPI formulation for human use. The operating parameters used during spray-drying were as follows: feed rate 3.0 g/min, inlet temperature 70° C., 0.7 mm nozzle, 1.5 mm nozzle-cap, compressed air at 800 L/min and drying air flow 35 m³/h. The apparatus was equipped with a B-296 dehumidifier (Büchi Labortechnik AG) to maintain the relative humidity at 50% HR during spray-drying.

The geometrical PSD of bulk cisplatin, cisplatin microparticles from the size-reduction process, and cisplatin dry powder formulation, was measured as suspended and individualized particles and was within the range of the present disclosure. This was done using a Mastersizer 3000 laser diffractometer (Malvern Instruments Ltd., Worcestershire, UK) connected to a Hydro MV dispenser equipped with a 40 W ultrasonic probe (Malvern Instruments Ltd.) as described in the Example 1.

Example 17.—Analysis of Deposition Rate of the Cisplatin Dry Powder Formulation Prepared According to Example 6 16

The formulations according to examples 16 have been analyzed regarding its in vitro pulmonary deposition pattern and FPF value.

The FPF—which is the percentage related to the recovered dose of cisplatin-based particles with an dae below 5 µm—and the aerodynamic PSD, characterized by the MMAD, were determined using a NGI (Copley Scientific, Nottingham, UK)—Apparatus E—as described in the European Pharmacopoeia 8.0. (2014). A mass of 20 mg of the DPI formulations (according to example 17), previously sieved through a 355 mm stainless steel mesh, was weighed in a size 3 HPMC capsule (Quali-V-I, Qualicaps, Madrid, Spain) and deposited in the NGI using RS.01 dry powder inhaler (RPC Plastiape, Osnago, Italy) mounted on the inhalation port with its adapter (n=3).

A deposition flow rate of 100±5 L/min measured using a DFM3 flow meter (Copley Scientific, Nottingham, UK) was obtained with two HCP5 air pumps (Copley Scientific, Nottingham, UK) connected in series to a TPK critical flow controller (Copley Scientific, Nottingham, UK).

At this flow rate, cut-off diameters were 6.12, 3.42, 2.18, 1.31, 0.72, 0.40 and 0.24 µm between each stage of the NGI. The critical flow controller was used to ensure a deposition time of 2.4 s at 100 L/min and a critical flow with a P3/P2 ratio<0.5, as required by the European Pharmacopoeia 8.0. (2014).

After impaction, the cisplatin mass deposited in the capsule, in the device, in the induction port, in the pre-separator, in the 7 stages and the MOC of the NGI were collected with DMF as the dilution phase and ultrasonicated for 30 min. The impacted mass in each stage was determined by quantification of the cisplatin content by the validated ETAAS method described by Levet et al (Levet et al, Int J Pharm 2016).

Results were then plotted in Copley Inhaler Testing Data Analysis Software1 (Copley Scientific, Nottingham, UK) to obtain the FPD below 5 µm. This was done from interpolation of the recovered mass vs. the cut-off diameter of the corresponding stage. The FPF was expressed as a percentage of the nominal dose.

The results obtained were in merge with those obtained in Example 3, demonstrating the superiority the cisplatin compositions disclosed in the present disclosure, compared to other triglyceride-based cisplatin DPI formulations in terms of pulmonary deposition.

Example 18.—Analysis of Dissolution Rate of Cisplatin from the Cisplatin Dry Powder Formulation Prepared According to Examples 16

Dissolution properties of the DPI formulation was established by applying an adaptation of the method described by Pilcer et al (Pilcer et al, J Pharm Sci 2013). A dissolution system (Copley Scientific, Nottingham, UK) specifically developed for DPI release profile studies was used with a method adapted from the "Paddle over Disc" (Eur.Ph. 7). To study the release profiles of the particles which deposit in the lungs, a fractionation of the cisplatin formulation was first performed with an NGI. The cup at stage 3 was chosen to be equipped with a removable disc insert to collect particles. Of particular interest, at the selected inhalation rate (100 L/min for 2.4 s), the cut-off diameters of stage 3 ranged between 2.18 and 3.42 µm, allowing the selection of particles targeting the lung from a capsule filled with an appropriate amount of formulations according to Example 16 to deposit about 2 mg cisplatin on stage 3. Then, the disc insert was covered with a polycarbonate membrane (0.4 µm pore size) (Merck Millipore) and put into a paddle dissolution apparatus (Erweka DT6; ERWEKA GmbH, Heusenstamm, Hesse, Germany) filled with 400 mL of mSLF (Son and McConville, 2009) —a medium that mimics the lungs electrolytic and surfactant composition.

Dissolution testing was realized in accordance with sink conditions, at 37±0.2° C., pH 7.35±0.05. Paddles, set at 25±2 mm between the blade and the center of the disk-assembly, were set at a rotating speed of 50±4 rpm. Sampling volumes of 2.0 mL were filtered through 0.22 mm pore size cellulose acetate syringe filters (VWR, Leuven, Belgium) at pre-established times between 2 min and 24 h, and replaced with 2.0 mL of free pre-heated mSLF.

At the end of the dissolution assay, the disk assembly was opened into the dissolution vessel and ultrasonicated for 30 min to establish the 100% cisplatin dissolution value.

Figure 7:
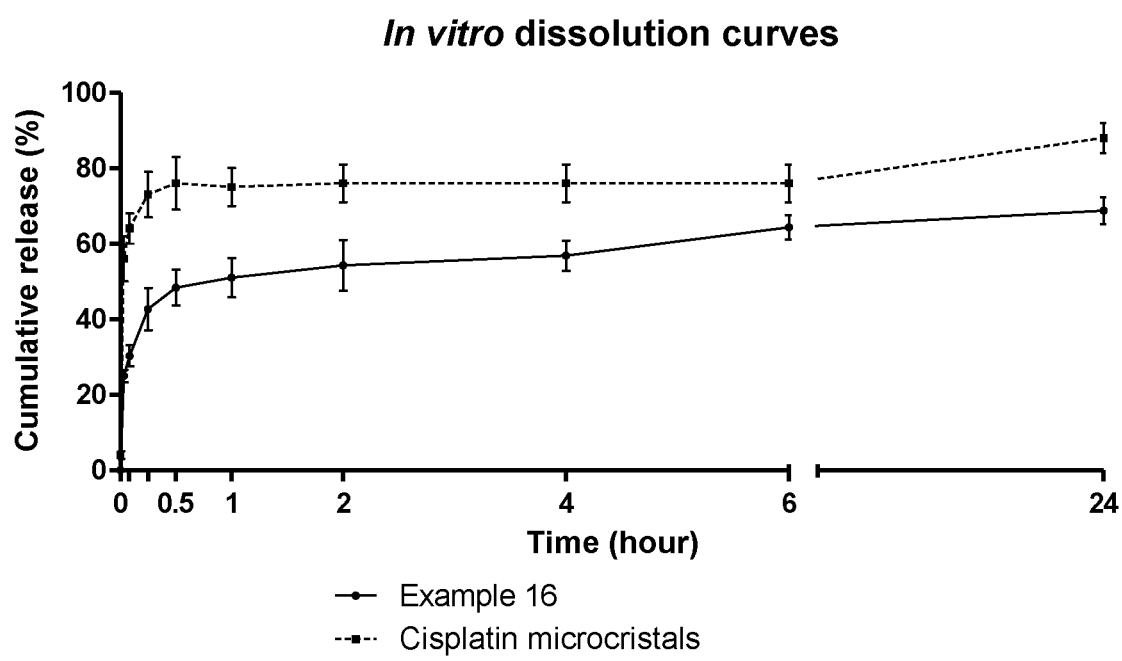
FIG. 7 presents the release profiles of cisplatin from the respirable fraction of the DPI formulation prepared according to Example 16, compared to the comparative formulation composed of cisplatin microparticles (mean±SD, n=3).

FIG. 7 presents the release profiles of cisplatin from the respirable fraction of the DPI formulation prepared according to Example 16, compared to the comparative formulation composed of cisplatin microparticles (mean±SD, n=3).

The similarity factor f2 was used to compare the two dissolution profiles (Shah et al, Pharm Res 1998). The curves were significantly different (f2<50). Moreover, the cumulative release values at all the timepoints from Example 16 were significantly lower compared to those from cisplatin microcrystals (p<0.05, t-test), e.g. at 4 h, respectively, 57±4% vs 76±5% (p<0.01), indicating a controlled release profile of cisplatin from a composition of the present disclosure.

Example 19.—Preparation of Budesonide Dry Powder Formulation for Inhalation n° 4

0.1500% w/v budesonide, 2.8215% w/v castor oil hydrogenated (BASF, Ludwigshafen, Germany) (or tristearin for the comparative examples BUD-TS4) and 0.0285% w/v TPGS (Sigma-Aldrich, St-Louis, USA) were solubilized in hot isopropanol (65° C.) under magnetic stirring and the hot solution was spray dried with a Mini-Spray Dryer B-290 (Büchi Labortechnik AG, Flawil, Switzerland) to obtain a DPI formulation for human use. The operating parameters used during spray-drying were as follows: feed rate 3.0 g/min, inlet temperature 70° C., 0.7 mm nozzle, 1.5 mm nozzle-cap, compressed air at 800 L/min and drying air flow 35 m$^3$/h. The apparatus was equipped with a B-296 dehumidifier (Büchi Labortechnik AG) to maintain the relative humidity at 50% HR during spray-drying.

Example 20.—Preparation of Budesonide Dry Powder Formulation for Inhalation n° 5

0.600% w/v budesonide, 2.376% w/v castor oil hydrogenated (BASF, Ludwigshafen, Germany) (or tristearin for the comparative examples BUD-TS5) and 0.024% w/v TPGS (Sigma-Aldrich, St-Louis, USA) were solubilized in hot isopropanol (65° C.) under magnetic stirring and the hot solution was spray dried with a Mini-Spray Dryer B-290 (Büchi Labortechnik AG, Flawil, Switzerland) to obtain a DPI formulation for human use. The operating parameters used during spray-drying were as follows: feed rate 3.0 g/min, inlet temperature 70° C., 0.7 mm nozzle, 1.5 mm nozzle-cap, compressed air at 800 L/min and drying air flow 35 m$^3$/h. The apparatus was equipped with a B-296 dehumidifier (Büchi Labortechnik AG) to maintain the relative humidity at 50% HR during spray-drying.

Example 21.—Preparation of Budesonide Dry Powder Formulation for Inhalation n° 6

1.500% w/v budesonide, 1.485% w/v castor oil hydrogenated (BASF, Ludwigshafen, Germany) and 0.015% w/v TPGS (Sigma-Aldrich, St-Louis, USA) were solubilized in hot isopropanol (65° C.) under magnetic stirring and the hot solution was spray dried with a Mini-Spray Dryer B-290 (Büchi Labortechnik AG, Flawil, Switzerland) to obtain a DPI formulation for human use. The operating parameters used during spray-drying were as follows: feed rate 3.0 g/min, inlet temperature 70° C., 0.7 mm nozzle, 1.5 mm nozzle-cap, compressed air at 800 L/min and drying air flow 35 m$^3$/h. The apparatus was equipped with a B-296 dehumidifier (Büchi Labortechnik AG) to maintain the relative humidity at 50% HR during spray-drying.

Example 22.—Analysis of Deposition Rate of the Budesonide Dry Powder Formulations Prepared According to Examples 19 and 20

The formulations according to examples 19 and 20 have been analyzed regarding its in vitro pulmonary deposition pattern and fine particle fraction value. Comparative examples of formulations 19 and 20, i.e. BUD-TS4 and BUD-TS5 respectively, were produced with tristearin (TS) (Tokyo Chemical Company, Tokyo, Japan) instead of castor oil hydrogenated following the same corresponding protocols.

The FPF—which is the percentage related to the recovered dose of budesonide-based particles with an dae below 5 µm—and the aerodynamic PSD, characterized by the MMAD, were determined using a NGI (Copley Scientific, Nottingham, UK)—Apparatus E—as described in the European Pharmacopoeia 8.0. (2014). A mass of 10 mg of the DPI formulations (according to examples 19 and 20 and comparative powders BUD-TS4 and BUD-TS5, previously sieved through a 355 mm stainless steel mesh, was weighed in a size 3 HPMC capsule (Quali-V-1, Qualicaps, Madrid, Spain) and deposited in the NGI using RS.01 dry powder inhaler (RPC Plastiape, Osnago, Italy) mounted on the inhalation port with its adapter (n=3).

A deposition flow rate of 100±5 L/min measured using a DFM3 flow meter (Copley Scientific, Nottingham, UK) was obtained with two HCP5 air pumps (Copley Scientific, Nottingham, UK) connected in series to a TPK critical flow controller (Copley Scientific, Nottingham, UK).

At this flow rate, cut-off diameters were 6.12, 3.42, 2.18, 1.31, 0.72, 0.40 and 0.24 µm between each stage of the NGI. The critical flow controller was used to ensure a deposition time of 2.4 s at 100 L/min and a critical flow with a P3/P2 ratio<0.5, as required by the European Pharmacopoeia 8.0. (2014).

After impaction, the budesonide mass deposited in the capsule, in the device, in the induction port, in the pre-separator, the 7 stages and the MOC of the NGI were collected with 0.5% w/v Poloxamer 407 in ultrapure water: isopropanol 60:40 (v/v) mixture as the dilution phase and ultrasonicated for 30 min at 60° C. The solutions were then filtrated through 0.45 µm pore size regenerated cellulose Minisart syringe filters (Sartorius Stedim Biotech GmbH, Germany). The impacted mass in each stage was determined by quantification of the budesonide content by a validated HPLC method. The chromatographic system (HP 1200 series, Agilent Technologies, Diegem, Belgium) was equipped with a quaternary pump, an auto sampler, and a diode array detector. The separations were performed on a reverse-phase Alltima C18 column (5 mm, 150 mm×4.6 mm) (Hichrom, Theale, UK). The mobile phase consisted of pH=3.20 phosphate buffer:acetonitrile (65:35 v/v), which was delivered at a flow rate of 1.5 mL/min. The quantification was performed at 245 nm. The volume injected was 100 µL, the temperature was set at 40° C., and the analysis run time was 22 min.

Results were then plotted in Copley Inhaler Testing Data Analysis Software1 (Copley Scientific, Nottingham, UK) to obtain the FPD below 5 µm. This was done from interpolation of the recovered mass vs. the cut-off diameter of the corresponding stage. The FPF was expressed as a percentage of the nominal dose.

Figure 8:
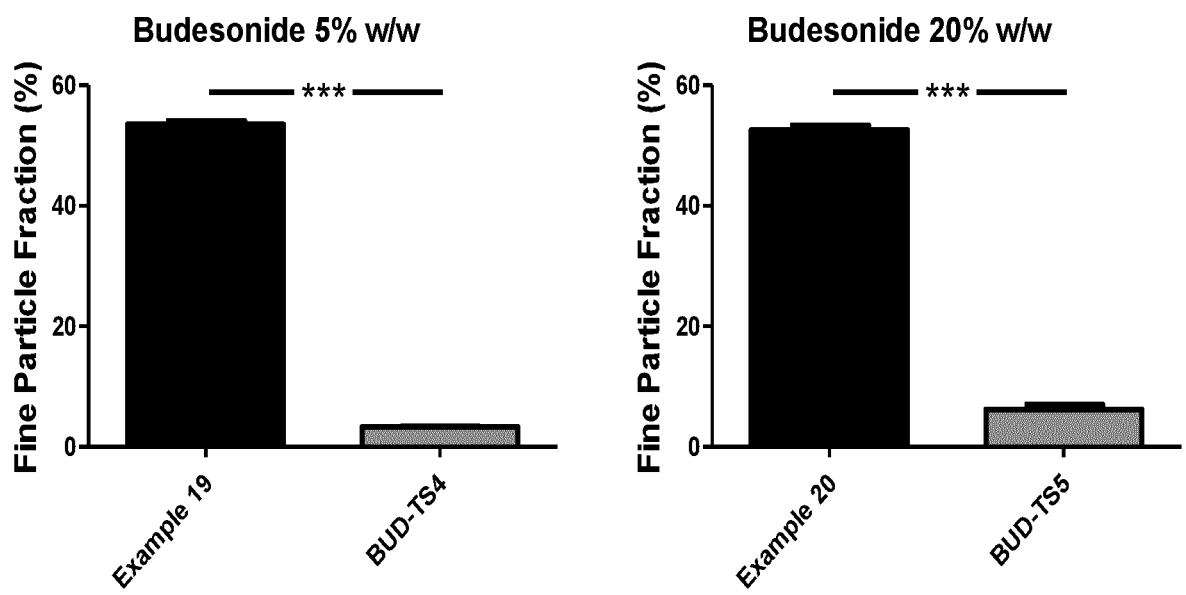
FIG. 8 presents FPF values of examples 19 and 20, compared to comparative examples BUD-TS4 and BUD-TS5 (mean±SD, n=3). (***) $p<0.001$, t-test, demonstrating the superiority the budesonide compositions disclosed in the present disclosure, compared to other triglyceride-based budesonide DPI formulations in terms of pulmonary deposition.

FIG. 8 presents FPF values of examples 19 and 20, compared to comparative examples BUD-TS4 and BUD-TS5 (mean±SD, n=3). (***) $p<0.001$, t-test, demonstrating the superiority the budesonide compositions disclosed in the present disclosure, compared to other triglyceride-based budesonide DPI formulations in terms of pulmonary deposition.

Example 23.—Analysis of Dissolution Rate of Budesonide from the Budesonide Dry Powder Formulations Prepared According to Examples 19, 20 and 21

Dissolution properties of the DPI formulations according to examples 19, 20 and 21 and a comparative budesonide powder (i.e. micronized budesonide) was established by applying an adaptation of the method described by Pilcer et al (Pilcer et al, J Pharm Sci 2013). The comparative micronized budesonide powder was produced by spray-drying (Mini-Spray Dryer B-290, Büchi Labortechnik AG, Flawil, Switzerland) a 3% w/v budesonide isopropanol solution to obtain a DPI formulation for human use.

A dissolution system (Copley Scientific, Nottingham, UK) specifically developed for DPI release profile studies was used with a method adapted from the "Paddle over Disc" (Eur.Ph. 7). To study the release profiles of the particles which deposit in the lungs, a fractionation of the budesonide formulation was first performed with an NGI. The cup at stage 2 was chosen to be equipped with a removable disc insert to collect particles. Of particular interest, at the selected inhalation rate (100 L/min for 2.4 s), the cut-off diameters of stage 2 ranged between 6.12 µm and 3.42 µm, allowing the selection of particles targeting the lung from a capsule filled with an appropriate amount of formulation (according to micronized budesonide and examples 20, 21 and 22) to deposit about 500 µg budesonide in stage 3. Then, the disc insert was covered with a polycarbonate membrane (0.4 µm pore size) (Merck Millipore) and put into a paddle dissolution apparatus (Erweka DT6; ERWEKA GmbH, Heusenstamm, Hesse, Germany) filled with 400 mL of 0.01 mM phosphate buffer saline (PBS) at pH 7.4.

Dissolution testing was realized in accordance with sink conditions, at 37±0.2° C., pH 7.35±0.05. Paddles, set at 25±2 mm between the blade and the center of the disk-assembly, were set at a rotating speed of 50±4 rpm. Sampling volumes of 2.0 mL were filtered through 0.22 mm pore size cellulose acetate syringe filters (VWR, Leuven, Belgium) at pre-established times between 2 min and 24 h, and replaced with 2.0 mL of free pre-heated PBS.

The 100% budesonide dissolution value correspond to the mass deposited in stage 3.

Figure 9:
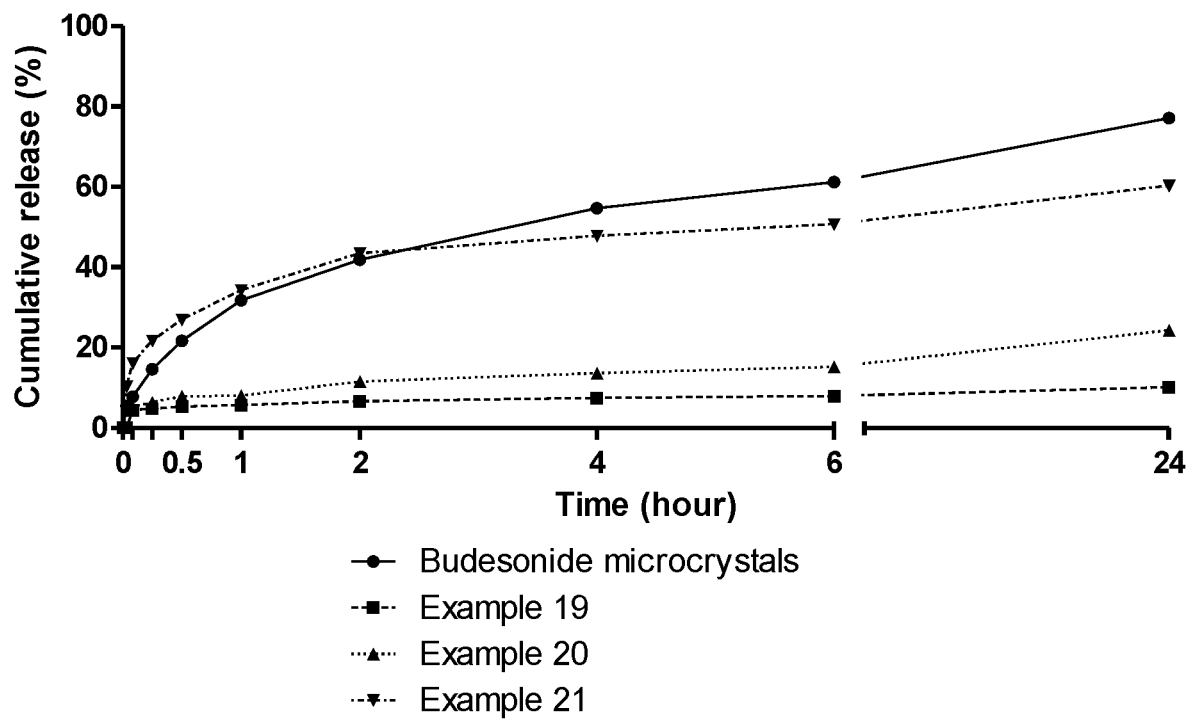
FIG. 9 presents the release profiles of budesonide from the respirable fraction of the micronized budesonide comparative example and the DPI formulations prepared according to Examples 19, 20 and 21 (n=1), indicating a controlled release profile of budesonide from compositions of the present disclosure and the possibility of modulating the release profile by modulating the drug/lipid ratio.

FIG. 9 presents the release profiles of budesonide from the respirable fraction of the micronized budesonide comparative example and the DPI formulations prepared according to Examples 19, 20 and 21 (n=1), indicating a controlled release profile of budesonide from compositions of the present disclosure and the possibility of modulating the release profile by modulating the drug/lipid ratio.

Example 24.—Preparation of Paclitaxel Dry Powder

Formulation for Inhalation n° 1 0.1500% w/v paclitaxel, 2.8215% w/v castor oil hydrogenated (BASF, Ludwigshafen, Germany) and 0.0285% w/v TPGS (Sigma-Aldrich, St-Louis, USA) were solubilized in hot ethanol (50° C.) under magnetic stirring and the hot solution was spray dried with a Mini-Spray Dryer B-290 (Büchi Labortechnik AG, Flawil, Switzerland) to obtain a DPI formulation for human use. The operating parameters used during spray-drying were as follows: feed rate 3.0 g/min, inlet temperature 70° C., 0.7 mm nozzle, 1.5 mm nozzle-cap, compressed air at 800 L/min and drying air flow 35 m³/h. The apparatus was equipped with a B-296 dehumidifier (Büchi Labortechnik AG) to maintain the relative humidity at 50% HR during spray-drying.

Example 25.—Preparation of Paclitaxel Dry Powder Formulation for Inhalation n° 2

0.600% w/v paclitaxel, 2.376% w/v castor oil hydrogenated (BASF, Ludwigshafen, Germany) and 0.024% w/v TPGS (Sigma-Aldrich, St-Louis, USA) were solubilized in hot ethanol (50° C.) under magnetic stirring and the hot solution was spray dried with a Mini-Spray Dryer B-290 (Büchi Labortechnik AG, Flawil, Switzerland) to obtain a DPI formulation for human use. The operating parameters used during spray-drying were as follows: feed rate 3.0 g/min, inlet temperature 70° C., 0.7 mm nozzle, 1.5 mm nozzle-cap, compressed air at 800 L/min and drying air flow 35 m³/h. The apparatus was equipped with a B-296 dehumidifier (Büchi Labortechnik AG) to maintain the relative humidity at 50% HR during spray-drying.

Example 26.—Preparation of Paclitaxel Dry Powder Formulation for Inhalation n° 3

1.500% w/v paclitaxel, 1.485% w/v castor oil hydrogenated (BASF, Ludwigshafen, Germany) and 0.015% w/v TPGS (Sigma-Aldrich, St-Louis, USA) were solubilized in hot ethanol (50° C.) under magnetic stirring and the hot solution was spray dried with a Mini-Spray Dryer B-290 (Büchi Labortechnik AG, Flawil, Switzerland) to obtain a DPI formulation for human use. The operating parameters used during spray-drying were as follows: feed rate 3.0 g/min, inlet temperature 70° C., 0.7 mm nozzle, 1.5 mm nozzle-cap, compressed air at 800 L/min and drying air flow 35 m³/h. The apparatus was equipped with a B-296 dehumidifier (Büchi Labortechnik AG) to maintain the relative humidity at 50% HR during spray-drying.

Example 27.—Preparation of Paclitaxel Dry Powder Formulation for Inhalation n° 4

2.700% w/v paclitaxel, 0.297% w/v castor oil hydrogenated (BASF, Ludwigshafen, Germany) and 0.003% w/v TPGS (Sigma-Aldrich, St-Louis, USA) were solubilized in hot ethanol (50° C.) under magnetic stirring and the hot solution was spray dried with a Mini-Spray Dryer B-290 (Büchi Labortechnik AG, Flawil, Switzerland) to obtain a DPI formulation for human use. The operating parameters used during spray-drying were as follows: feed rate 3.0 g/min, inlet temperature 70° C., 0.7 mm nozzle, 1.5 mm nozzle-cap, compressed air at 800 L/min and drying air flow 35 m³/h. The apparatus was equipped with a B-296 dehumidifier (Büchi Labortechnik AG) to maintain the relative humidity at 50% HR during spray-drying.

Example 28.—Preparation of Paclitaxel Dry Powder Formulation for Inhalation n° 5

1.50% w/v paclitaxel, 1.35% w/v castor oil hydrogenated (BASF, Ludwigshafen, Germany) and 0.15% w/v TPGS (Sigma-Aldrich, St-Louis, USA) were solubilized in hot ethanol (50° C.) under magnetic stirring and the hot solution was spray dried with a Mini-Spray Dryer B-290 (Büchi Labortechnik AG, Flawil, Switzerland) to obtain a DPI formulation for human use. The operating parameters used during spray-drying were as follows: feed rate 3.0 g/min, inlet temperature 70° C., 0.7 mm nozzle, 1.5 mm nozzle-cap, compressed air at 800 L/min and drying air flow 35 m³/h. The apparatus was equipped with a B-296 dehumidifier (Büchi Labortechnik AG) to maintain the relative humidity at 50% HR during spray-drying.

Example 29.—Preparation of Paclitaxel Dry Powder Formulation for Inhalation n° 6

1.5% w/v paclitaxel, 1.2% w/v castor oil hydrogenated (BASF, Ludwigshafen, Germany) and 0.3% w/v TPGS (Sigma-Aldrich, St-Louis, USA) were solubilized in hot ethanol (50° C.) under magnetic stirring and the hot solution was spray dried with a Mini-Spray Dryer B-290 (Büchi Labortechnik AG, Flawil, Switzerland) to obtain a DPI formulation for human use. The operating parameters used during spray-drying were as follows: feed rate 3.0 g/min, inlet temperature 70° C., 0.7 mm nozzle, 1.5 mm nozzle-cap, compressed air at 800 L/min and drying air flow 35 m³/h. The apparatus was equipped with a B-296 dehumidifier (Büchi Labortechnik AG) to maintain the relative humidity at 50% HR during spray-drying.

Example 30.—Preparation of Paclitaxel Dry Powder Formulation for Inhalation n° 7

1.500% w/v paclitaxel, 1.485% w/v castor oil hydrogenated (BASF, Ludwigshafen, Germany), 0.015% w/v TPGS (Sigma-Aldrich, St-Louis, USA) and 0.3% w/v L-leucine (Sigma-Aldrich) were solubilized in hot ethanol (50° C.) under magnetic stirring and the hot solution was spray dried with a Mini-Spray Dryer B-290 (Büchi Labortechnik AG, Flawil, Switzerland) to obtain a DPI formulation for human use. The operating parameters used during spray-drying were as follows: feed rate 3.0 g/min, inlet temperature 70° C., 0.7 mm nozzle, 1.5 mm nozzle-cap, compressed air at 800 L/min and drying air flow 35 m³/h. The apparatus was equipped with a B-296 dehumidifier (Büchi Labortechnik AG) to maintain the relative humidity at 50% HR during spray-drying.

Example 31.—Preparation of Budesonide Dry Powder Formulation for Inhalation n° 7

Budesonide dry powder formulation for inhalation n° 4 was first prepared according to Example 19. An amount of 10 g budesonide dry powder formulation for inhalation n° 4 and 30 g lactose (Respitose® SV003, DFE Pharma, Goch, Germany) were then blended to homogeneity in a Turbula® mixer (Willy A. Bachofen AG, Muttenz, Switzerland) to obtain a carrier-based dry powder formulation for inhalation.

It should be understood that the present disclosure is not limited to the described embodiments and that variations can be applied without going outside of the scope of the appended claims.

The invention claimed is:

1. A dry powder inhalation formulation comprising at least one active pharmaceutical ingredient (API) and a lipid matrix comprising a mixture of monohydroxystearin, dihydroxystearin, and trihydroxystearin, wherein said dry powder inhalation formulation has a weight ratio between said at least one API and said lipid matrix: between 0.1/99.9 and 88/12.

2. The dry powder inhalation formulation according to claim 1, having a weight ratio between said at least one API and said lipid matrix: API/lipid matrix comprised between 10/90 and 88/12.

3. The dry powder inhalation formulation according to claim 1, the lipid matrix consists of hydrogenated castor oil.

4. The dry powder inhalation formulation according to claim 1, wherein said API is a small chemical molecule having a solubility in alcohols of at least 0.1 w %/v.

5. The dry powder inhalation formulation according to claim 1, wherein said API is a small chemical molecule having a solubility in alcohols less than 0.5 w %/v.

6. The dry powder inhalation formulation according to claim 1, wherein said API is a macromolecule.

7. The dry powder inhalation formulation according to claim 1, further comprising a prolonged lung retention excipient.

8. The dry powder inhalation formulation according to claim 7, wherein said prolonged lung retention excipient is a PEGylated excipient and is present at an amount comprised between 1 wt % to 20 wt % relative to the total weight of said dry powder inhalation formulation.

9. The dry powder inhalation formulation according to claim 8, wherein said PEGylated excipient is derived from one of vitamin E, phospholipids, and distearoyl phosphoethanolamine polyethylene glycol 2000 (DSPE-mPEG-2000).

10. The dry powder inhalation formulation according to claim 1, wherein said formulation has a geometric particle size distribution (PSD) d50 lower than or equal to 30 μm.

11. The dry powder inhalation formulation according to claim 1, wherein said formulation has a geometric particle size distribution (PSD) d90 lower than or equal to 60 μm.

12. The dry powder inhalation formulation according to claim 1, wherein said formulation has a volume mean diameter D[4,3] lower than or equal to 40 μm.

13. The dry powder inhalation formulation according to claim 1, further comprising an excipient that alters or changes at least one of physicochemical properties and aerodynamic properties, wherein the excipient is a disaccharide.

14. The dry powder inhalation formulation according to claim 1, under the form of particles having a mass median aerodynamic diameter (MMAD) lower than or equal to 6 km.

15. A dry powder inhalation formulation comprising at least one active pharmaceutical ingredient (API) and a lipid matrix comprising a mixture of monohydroxystearin, dihydroxystearin, trihydroxystearin, wherein said dry powder inhalation formulation has a weight ratio between said at least one API and said lipid matrix: between 40/60 and 60/40, wherein said API is cisplatin, said formulation being in a capsule, configured to be used in at least one of a dry powder inhaler, a hermetic dry powder inhaler, and a disposable dry powder inhaler.

16. The dry powder inhalation formulation according to claim 1, wherein said API is a small chemical molecule having at least one of a bronchodilator activity, a glucocorticoid, an anti-inflammatory activity, and an anti-infection activity.

17. The dry powder inhalation formulation according to claim 1, wherein said API is an anti-neoplastic agent.

18. The dry powder inhalation formulation according to claim 17, wherein said anti-neoplastic agent is one of cisplatin, carboplatin, oxaliplatin, docetaxel, paclitaxel, pemetrexed, etoposide, and vinorelbine.

19. The dry powder inhalation formulation according to claim 1, under the form of an oral dry powder inhalation formulation.

20. A dry powder inhalation formulation comprising at least one active pharmaceutical ingredient (API) and a lipid matrix comprising a mixture of monohydroxystearin, dihydroxystearin, trihydroxystearin, wherein said dry powder inhalation formulation has a weight ratio between said at least one API and said lipid matrix: between 40/60 and 60/40, wherein said API is cisplatin.

21. The dry powder inhalation formulation according to claim 1, having a weight ratio between said at least one API and said lipid matrix: API/lipid matrix comprised between 15/85 and 85/15.

* * * * *